US008853435B1

(12) United States Patent
Tomkins et al.

(10) Patent No.: US 8,853,435 B1
(45) Date of Patent: Oct. 7, 2014

(54) PARTIAL NEUTRALIZATION OF FREE FATTY ACID MIXTURES WITH MAGNESIUM, LIVESTOCK FEED COMPOSITIONS INCLUDING THEM, AND METHODS OF MAKING SAME

(75) Inventors: Trevor Tomkins, Carpentersville, IL (US); Steven Lamb, Shakopee, MN (US)

(73) Assignee: Milk Specialties Company, Carpentersville, IL (US)

( * ) Notice: Subject to any disclaimer, the term of this patent is extended or adjusted under 35 U.S.C. 154(b) by 0 days.

(21) Appl. No.: 13/475,455

(22) Filed: May 18, 2012

Related U.S. Application Data

(60) Provisional application No. 61/488,282, filed on May 20, 2011.

(51) Int. Cl.
| | |
|---|---|
| *C07C 51/00* | (2006.01) |
| *A23D 9/007* | (2006.01) |
| *C07C 51/41* | (2006.01) |
| *A23K 1/16* | (2006.01) |

(52) U.S. Cl.
CPC .............. *C07C 51/412* (2013.01); *A23K 1/164* (2013.01)
USPC ............ 554/156; 554/124; 554/157; 426/601

(58) Field of Classification Search
CPC ..... C07C 51/412; A23L 1/3006; A23K 1/164
See application file for complete search history.

(56) References Cited

U.S. PATENT DOCUMENTS

| | | | | |
|---|---|---|---|---|
| 2,890,232 | A | * | 6/1959 | Rogers, Jr. et al. ............. 554/75 |
| 3,376,327 | A | * | 4/1968 | Freeland ....................... 554/156 |
| 3,519,571 | A | * | 7/1970 | Szczepanek et al. ..... 252/400.51 |
| 3,803,188 | A | * | 4/1974 | Scott ............................... 554/75 |
| 4,016,296 | A | | 4/1977 | DeSantis |
| 4,062,988 | A | | 12/1977 | DeSantis |
| 4,198,294 | A | | 4/1980 | Deane |
| 4,221,818 | A | | 9/1980 | Schroeder |
| 4,307,027 | A | * | 12/1981 | Borzelli et al. ................. 554/75 |
| 4,642,317 | A | | 2/1987 | Palmquist et al. |
| 4,826,694 | A | | 5/1989 | McAskie |
| 4,853,233 | A | | 8/1989 | McAskie |
| 4,909,138 | A | | 3/1990 | McAskie |
| 5,234,701 | A | | 8/1993 | Cummings et al. |

(Continued)

OTHER PUBLICATIONS

Elliott, J.P., et al., Digestibility and effects of three forms of mostly saturated fatty acids, 1994, J. Dairy Sci., vol. 77, No. 3, pp. 789-798.*

*Primary Examiner* — Yate K Cutliff
(74) *Attorney, Agent, or Firm* — Mueting, Raasch & Gebhardt, P.A.

(57) ABSTRACT

The present invention includes a nutritional supplement composition that may be used for livestock and the like, as well as to a livestock feed mixture containing same. Also included are methods of preparing the nutritional supplement composition, the livestock feed mixture, as well as methods of providing nutrition to livestock and the like. The livestock feed composition comprises: (a) a solid particulate livestock feed material and (b) a solidified particulate mixture of (i) free fatty acid and (ii) a magnesium salt of a fatty acid, the magnesium salt of a fatty acid being present in an amount in the range of from about 25% to about 55% of the amount of the free fatty acid based upon the theoretical requirement to accomplish the total neutralization of all of fatty acid present.

16 Claims, 24 Drawing Sheets

(56) References Cited

U.S. PATENT DOCUMENTS

| | | |
|---|---|---|
| 5,382,678 A | 1/1995 | Vinci et al. |
| 5,783,714 A | 7/1998 | McKenna et al. |
| 6,229,031 B1 | 5/2001 | Strohmaier et al. |
| 6,576,667 B2 | 6/2003 | Strohmaier et al. |
| 6,656,494 B1 * | 12/2003 | Nakata et al. ............. 424/442 |
| 6,774,252 B2 | 8/2004 | Strohmaier et al. |
| 7,318,943 B2 | 1/2008 | Baricco et al. |
| 2009/0220638 A1 | 9/2009 | Perez |
| 2009/0297686 A1 * | 12/2009 | Pablos Perez ............. 426/601 |

* cited by examiner

EB-Hardening: Compression Testing

FIG. 9

| Exp # | EBH-100503 | AV Analysis | | | | | | |
|---|---|---|---|---|---|---|---|---|
| SOP | Boscobel Procedure Number: 7.1.14 -02 (Issue Date: July 15,2001) | | | | | | | |
| | All Definitions, Materials, Equipment, Reagents... are specified in the detailed SOP | | | | | | | |
| Procedure | 1 | Record Sample Descriptor and exact sample weight in calculator table to left | | | | | | |
| | 2 | Weigh 0.35 gm sample to nearest 0.0001 gm into 500 ml Erln flask | | | | | | |
| | 3 | Add 75 ml of Neutralized Alcohol + Phenolphthalein | | | | | | |
| | 4 | Record starting ml of 0.1 N NaOH in burette in calculator table below | | | | | | |
| | 5 | Add 2 drops of Phenolphthalein indicator and titrate immediately, while swirling, with 0.1N NaOH to the first pink color that persists for 30 seconds | | | | | | |
| | 6 | Record final ml of 0.1 N NaOH in burette in calculator table to left | | | | | | |

| Sample ID | Sample Wt (grams) | Starting NaOH (ml) | Ending NaOH (ml) | Added NaOH (ml) | AV (mg KOH/gm) | %FFA (as Oleic) | % Neut (% Magnif) | % Neut (% Magnif) |
|---|---|---|---|---|---|---|---|---|
| 422 | 0.3583 | 6.90 | 19.45 | 12.55 | 196.5 | 98.9 | | |
| 422 | 0.3641 | 19.70 | 32.75 | 13.05 | 201.1 | 101.2 | | |
| 422 | 0.3684 | 23.95 | 36.00 | 12.05 | 183.5 | 92.4 | | |
| Average | | | | | 193.7 | 97.5 | | |
| Stdev | | | | | 9.1 | 4.6 | | |
| CV | | | | | 4.71% | 4.71% | | |
| 7916 | 0.3713 | 25.10 | 41.30 | 16.20 | 244.8 | 123.2 | | |
| 7916 | 0.3608 | 5.00 | 20.80 | 15.80 | 245.7 | 123.7 | | |
| 7916 | 0.3526 | 21.35 | 36.10 | 14.75 | 234.7 | 118.2 | | |
| 7916 | 0.3519 | 25.10 | 39.74 | 14.64 | 233.4 | 117.5 | | |
| Average | | | | | 237.9 | 119.8 | | |
| Stdev | | | | | 6.7 | 3.4 | | |
| CV | | | | | 2.83% | 2.83% | | |
| 0Hr Mix (no Mag) | 0.3583 | 11.90 | 24.90 | 13.00 | 204.7 | 103.1 | | |
| 0Hr Mix (no Mag) | 0.3499 | 8.75 | 21.45 | 12.70 | 203.6 | 102.5 | | |
| 0Hr Mix (no Mag) | | | | | | | | |
| Average | | | | | 204.2 | 102.8 | | |
| Stdev | | | | | 0.8 | 0.4 | | |
| CV | | | | | 0.37% | 0.37% | | |
| I2 | 0.3490 | 1.10 | 12.50 | 11.40 | 183.2 | 92.3 | 10.24 | |
| I2 | 0.3526 | 24.20 | 36.10 | 11.90 | 189.3 | 95.3 | 7.26 | 8.75 |
| I4 | 0.3534 | 12.85 | 24.60 | 11.75 | 186.5 | 93.9 | 8.64 | |
| I4 | 0.3522 | 24.80 | 36.45 | 11.65 | 185.6 | 93.4 | 9.10 | 8.87 |
| J2 | 0.3532 | 5.45 | 17.05 | 11.60 | 184.2 | 92.8 | 9.75 | |
| J2 | 0.3503 | 17.25 | 28.90 | 11.65 | 186.6 | 93.9 | 8.61 | 9.18 |
| J4 | 0.3500 | 29.95 | 41.50 | 11.55 | 185.1 | 93.2 | 9.32 | |
| J4 | 0.3512 | 21.40 | 33.00 | 11.60 | 185.3 | 93.3 | 9.24 | 9.28 |
| K2 | 0.3526 | 2.40 | 13.95 | 11.55 | 183.6 | 92.5 | 9.99 | |
| K2 | 0.3554 | 14.10 | 25.75 | 11.65 | 183.9 | 92.6 | 9.92 | 9.96 |
| K4 | 0.3499 | 26.10 | 37.10 | 11.00 | 176.4 | 88.8 | 13.61 | |
| K4 | 0.3492 | 37.15 | 48.25 | 11.10 | 178.3 | 89.8 | 12.65 | 13.13 |
| L2 | 0.3547 | 0.60 | 12.00 | 11.40 | 180.3 | 90.8 | 11.68 | |
| L2 | 0.3509 | 12.25 | 22.95 | 10.70 | 171.1 | 86.1 | 16.21 | 13.94 |
| L4 | 0.3564 | 23.25 | 34.90 | 11.65 | 183.4 | 92.3 | 10.18 | |
| L4 | 0.3527 | 35.25 | 46.50 | 11.25 | 178.9 | 90.1 | 12.35 | 11.26 |

FIG. 10

| | | | | Experiment Number: EBH-100503 | 85%422-8%7916-3.0, 3.5, 4.0, 4.5 -Wt% Mag- 93HR325, 300F | |
|---|---|---|---|---|---|---|
| Notebook Reference: | | | | | | |
| Objective: | | | | Determine Onset MP and Hardness Profile for 92%422-8%7916+Mag | Enter %Mag | 98.0% |
| Materials: I | 368.0 | gm | 422 | | Enter AV-422 | 193.7 (mgKOH/gmFA) |
| | 32.00 | gm | 7916 | | Enter AV-3198 | 257.9 (mgKOH/gmFA) |
| | | | | | Enter AV- #3 | |
| | | | | | Wt % Mag | 3.04% |
| | 12.54 | gm | MagChem 40 Mag | | Target % Neutralization | 43.55% |
| Materials: J | 368.0 | gm | 422 | | Enter AV-422 | 193.7 (mgKOH/gmFA) |
| | 32.00 | gm | 7916 | | Enter AV-3198 | 257.9 (mgKOH/gmFA) |
| | | | | | Enter AV- #3 | |
| | | | | | Enter AV - #4 | 3.54% |
| | 14.70 | gm | MagChem 40 Mag | | Target % Neutralization | 51.05% |
| Materials: K | 368.0 | gm | 422 | | Enter AV-422 | 193.7 (mgKOH/gmFA) |
| | 32.00 | gm | 7916 | | Enter AV-3198 | 257.9 (mgKOH/gmFA) |
| | | | | | Enter AV- #3 | |
| | | | | | Enter AV - #4 | 4.05% |
| | 16.87 | gm | MagChem 40 Mag | | Target % Neutralization | 58.60% |
| Materials: L | 368.0 | gm | 422 | | Enter AV-422 | 193.7 (mgKOH/gmFA) |
| | 32.00 | gm | 7916 | | Enter AV-3198 | 257.9 (mgKOH/gmFA) |
| | | | | | Enter AV- #3 | |
| | | | | | Enter AV - #4 | 4.50% |
| | 18.83 | gm | MagChem 40 Mag | | Target % Neutralization | 65.40% |
| Protocol: | For I, J, K and L Materials Above | | | | | |
| | | | Melt 422 + 7916 in 2 liter Beaker Reactor on hot plate with mixing | | | |
| | | | Take sample of melted mixture for 0Hr AV analysis | | | |
| | | | Heat to 220-240F | | | |
| | | | Stabilize temperature at 240F | | | |
| | | | Add Mag SLOWLY (use seive) into vortex with vigorous mixing and control temp to 300F | | | |
| | | | Take samples at 2 and 4 hrs after Mag addition and do AV analysis | | | |
| | | | Do MP and Hardness on 2 and 4 hr samples | | | |

FIG. 11

| EBH-100503 | 65%422-8%7916-3.0, 3.5, 4.0, 4.5 -Wt% Mag- 93HR325, 300F | | |
|---|---|---|---|
| Sample | Description | Observations/Comments | MP1-C Onset |
| I2 | 2hr-3.0 Wt% Mag | sweating at 60, bleeding at 65 | 65.0 |
| J2 | 2hr-3.5 Wt% Mag | sweating at 60, bleeding at 65 mostly melted at 70, liquid at 75 | 65.0 |
| K2 | 2hr-4.0 Wt% Mag | sweating at 60, bleeding at 65 mostly melted at 70, liquid at 75 | 65.0 |
| L2 | 2hr-4.5 Wt% Mag | sweating at 60, bleeding at 65/70, mostly melted at 75, liquid 80 | 70.0 |
| I4 | 4hr-3.0 Wt% Mag | sweating at 65, bleeding at 670, melted at 75, liquid 80 | 70.0 |
| J4 | 4hr-3.5 Wt% Mag | sweating at 65, bleeding at 670, melted at 75, liquid 80 | 75.0 |
| K4 | 4hr-4.0 Wt% Mag | sweating at 65, bleeding at 670, melted at 75, liquid 80 | 75.0 |
| L4 | 4hr-4.5 Wt% Mag | sweating at 65, bleeding at 670, melted at 75, liquid 80 | 75.0 |

| Sample | Description | Observations/Comments | MP1-F Onset |
|---|---|---|---|
| I2 | 2hr-3.0 Wt% Mag | sweating at 60, bleeding at 65 | 149.0 |
| J2 | 2hr-3.5 Wt% Mag | sweating at 60, bleeding at 65 mostly melted at 70, liquid at 75 | 149.0 |
| K2 | 2hr-4.0 Wt% Mag | sweating at 60, bleeding at 65 mostly melted at 70, liquid at 75 | 149.0 |
| L2 | 2hr-4.5 Wt% Mag | sweating at 60, bleeding at 65/70, mostly melted at 75, liquid 80 | 158.0 |
| I4 | 4hr-3.0 Wt% Mag | sweating at 65, bleeding at 670, melted at 75, liquid 80 | 158.0 |
| J4 | 4hr-3.5 Wt% Mag | sweating at 65, bleeding at 670, melted at 75, liquid 80 | 167.0 |
| K4 | 4hr-4.0 Wt% Mag | sweating at 65, bleeding at 670, melted at 75, liquid 80 | 167.0 |
| L4 | 4hr-4.5 Wt% Mag | sweating at 65, bleeding at 670, melted at 75, liquid 80 | 167.0 |

FIG. 12

| EBH-100503 | 85%422-8%7916-3.0, 3.5, 4.0, 4.5 -Wt% Mag- 93HR325, 300F | | Shore A Hardness at Temperature (C) | | | | | | | | | | |
|---|---|---|---|---|---|---|---|---|---|---|---|---|---|
| Sample | Description | Observation & Comments | 30 | 35 | 40 | 45 | 50 | 55 | 60 | 65 | 70 | 75 | 80 |
| I2 | 2hr-3.0 Wt% Mag | | x | x | x | 82.0 | 64.0 | 56.0 | 52.0 | 35.0 | 23.0 | 6.0 | <5 |
| J2 | 2hr-3.5 Wt% Mag | | x | x | x | 82.0 | 75.0 | 68.0 | 60.0 | 47.0 | 28.0 | 10.0 | <5 |
| K2 | 2hr-4.0 Wt% Mag | | x | x | x | 83.0 | 77.0 | 69.0 | 62.0 | 48.0 | 29.0 | 12.0 | <5 |
| L2 | 2hr-4.5 Wt% Mag | | x | x | x | 85.0 | 80.0 | 72.0 | 63.0 | 49.0 | 30.0 | 14.0 | <5 |
| I4 | 4hr-3.0 Wt% Mag | | x | x | x | 84.0 | 70.0 | 63.0 | 58.0 | 38.0 | 25.0 | 6.0 | <5 |
| J4 | 4hr-3.5 Wt% Mag | | x | x | x | 86.0 | 78.0 | 74.0 | 63.0 | 53.0 | 31.0 | 10.0 | <5 |
| K4 | 4hr-4.0 Wt% Mag | | x | x | x | 94.0 | 82.0 | 78.0 | 68.0 | 54.0 | 32.0 | 14.0 | <5 |
| L4 | 4hr-4.5 Wt% Mag | | x | x | x | 96.0 | 86.0 | 78.0 | 67.0 | 53.0 | 31.0 | 13.0 | <5 |

| | | | | | Shore A Hardness at Temperature (F) | | | | | | | | |
|---|---|---|---|---|---|---|---|---|---|---|---|---|---|
| Sample | Description | Observation & Comments | 86 | 95 | 104 | 113 | 122 | 131 | 140 | 149 | 158 | 167 | 176 |
| I2 | 2hr-3.0 Wt% Mag | | x | x | x | 82.0 | 64.0 | 56.0 | 52.0 | 35.0 | 23.0 | 6.0 | <5 |
| J2 | 2hr-3.5 Wt% Mag | | x | x | x | 82.0 | 75.0 | 68.0 | 60.0 | 47.0 | 28.0 | 10.0 | <5 |
| K2 | 2hr-4.0 Wt% Mag | | x | x | x | 83.0 | 77.0 | 69.0 | 62.0 | 48.0 | 29.0 | 12.0 | <5 |
| L2 | 2hr-4.5 Wt% Mag | | x | x | x | 85.0 | 80.0 | 72.0 | 63.0 | 49.0 | 30.0 | 14.0 | <5 |
| I4 | 4hr-3.0 Wt% Mag | | x | x | x | 84.0 | 70.0 | 63.0 | 58.0 | 38.0 | 25.0 | 6.0 | <5 |
| J4 | 4hr-3.5 Wt% Mag | | x | x | x | 86.0 | 78.0 | 74.0 | 63.0 | 53.0 | 31.0 | 10.0 | <5 |
| K4 | 4hr-4.0 Wt% Mag | | x | x | x | 94.0 | 82.0 | 78.0 | 68.0 | 54.0 | 32.0 | 14.0 | <5 |
| L4 | 4hr-4.5 Wt% Mag | | x | x | x | 96.0 | 86.0 | 78.0 | 67.0 | 53.0 | 31.0 | 13.0 | <5 |

|  | Magox feed grade (100 mesh) | Premier Chemicals Magox feed grade (10 mesh) | Magox 93HR Block Grade | MagChem MagChem 40 |
|---|---|---|---|---|
| CaO | 5.73% | 4.03% | 3.98% | 0.75% |
| Mag | 87.97% | 91.74% | 93.27% | 98.53% |
| Mg | 53.34% | 56.8 | | |

FIG. 18

| Exp # | EBH-150421 | AV Analysis | | | | | | |
|---|---|---|---|---|---|---|---|---|
| SOP | Boscobel Procedure Number: 7.1.14 -02 (Issue Date: July 19,2001) | | | | | | | |
| | All Definitions, Materials, Equipment, Reagents... are specified in the detailed SOP | | | | | | | |
| Procedure | 1 | Record Sample Descriptor and exact sample weight in calculator table to left | | | | | | |
| | 2 | Weigh 0.35 gm sample to nearest 0.0001 gm into 500 ml Erln flask | | | | | | |
| | 3 | Add 75 ml of Neutralized Alcohol + Phenolphthalein | | | | | | |
| | 4 | Record starting ml of 0.1 N NaOH in burette in calculator table below | | | | | | |
| | 5 | Add 2 drops of Phenolphthalein indicator and titrate immediately, while swirling, with 0.1N NaOH to the first pink color that persists for 30 seconds | | | | | | |
| | 6 | Record final ml of 0.1 N NaOH in burette in calculator table to left | | | | | | |

| Sample ID | Sample Wt (grams) | Starting NaOH (ml) | Ending NaOH (ml) | Added NaOH (ml) | AV (mg KOH/gm) | %FFA (as Oleic) | % Neut (% Magnif) | % Neut (% Magnif) |
|---|---|---|---|---|---|---|---|---|
| 422 | 0.3583 | 6.90 | 19.45 | 12.55 | 196.5 | 98.9 | | |
| 422 | 0.3941 | 19.70 | 32.75 | 13.05 | 201.1 | 101.2 | | |
| 422 | 0.3864 | 23.95 | 36.00 | 12.05 | 188.5 | 92.4 | | |
| Average | | | | | 193.7 | 97.5 | | |
| Stdev | | | | | 9.1 | 4.6 | | |
| CV | | | | | 4.71% | 4.71% | | |
| 7916 | 0.3713 | 25.10 | 41.30 | 16.20 | 244.8 | 123.2 | | |
| 7916 | 0.3908 | 5.90 | 20.80 | 15.90 | 245.7 | 123.7 | | |
| 7916 | 0.3525 | 21.35 | 36.10 | 14.75 | 233.7 | 118.2 | | |
| 7916 | 0.3519 | 25.10 | 39.74 | 14.64 | 233.4 | 117.5 | | |
| Average | | | | | 239.6 | 120.7 | | |
| Stdev | | | | | 239.4 | 120.0 | | |
| CV | | | | | 236.5 | 119.1 | | |
| F2 | 0.3506 | 35.10 | 44.40 | 9.30 | 148.7 | 74.9 | 27.34 | |
| F3 | 0.3551 | 37.10 | 46.40 | 9.30 | 146.9 | 74.0 | 28.22 | 27.78 |
| F4 | | | | | | #VALUE! | | |
| F4 | | | | | | #VALUE! | #VALUE! | |
| G2 | | | | | | #VALUE! | | |
| G3 | | | | | | #VALUE! | #VALUE! | |
| G4 | | | | | | #VALUE! | | |
| G4 | | | | | | #VALUE! | #VALUE! | |
| H2 | | | | | | #VALUE! | | |
| H3 | | | | | | #VALUE! | #VALUE! | |
| H4 | | | | | | #VALUE! | | |
| H4 | | | | | | #VALUE! | #VALUE! | |
| W0 | 0.3563 | 11.90 | 24.90 | 13.00 | 204.7 | 103.1 | | |
| W0 | 0.3499 | 8.75 | 21.45 | 12.70 | 203.6 | 102.5 | | |

| EBH-100421 | 85%423-6%7916, 60-70-80% Neutralization with Mag(MagChem40)-300F | | |
|---|---|---|---|
| Sample | Description | Observations/Comments | MP1-C Onset |
| F2 | 2hr-80%Mg-300F | gummy/sticky at 75, never melted just became molten | 90.0 |
| G2 | 2hr-100%Mg-300F | | |
| H2 | 2hr-120%Mg-300F | | |
| | | | |
| F2 | 4hr-80%Mg-300F | | |
| G2 | 4hr-100%Mg-300F | | |
| H2 | 4hr-120%Mg-300F | | |

| Sample | Description | Observations/Comments | MP1-F Onset |
|---|---|---|---|
| F2 | 2hr-80%Mg-300F | gummy/sticky at 75, never melted just became molten | 194.0 |
| G2 | 2hr-100%Mg-300F | | |
| H2 | 2hr-120%Mg-300F | | |
| | | | |
| F2 | 4hr-80%Mg-300F | | |
| G2 | 4hr-100%Mg-300F | | |
| H2 | 4hr-120%Mg-300F | | |

FIG. 21

| EBH-100421 Sample | 88%422-8%7918, 60-70-80% Neutralization with Mag(MagChem40)-300F Description | Observations Comments | Shore A Hardness at Temperature (C) | | | | | | | | | | | |
|---|---|---|---|---|---|---|---|---|---|---|---|---|---|
| | | | 30 | 35 | 40 | 45 | 50 | 55 | 60 | 65 | 70 | 75 | 80 | 85 | 90 |
| F2 | 2hr-80%Mg-300F | | X | X | X | 75.0 | 70.0 | 65.0 | 50.0 | 40.0 | 30.0 | 8.0 | <5 | <5 | gooey |
| G2 | 2hr-100%Mg-300F | | | | | | | | | | | | | | |
| H2 | 2hr-120%Mg-300F | | | | | | | | | | | | | | |
| | | | | | | | | | | | | | | | |
| F4 | 4hr-80%Mg-300F | | X | X | X | 73.0 | 70.0 | 63.0 | 47.0 | 40.0 | 25.0 | 8.0 | <5 | <5 | gooey |
| G4 | 4hr-100%Mg-300F | | | | | | | | | | | | | | |
| H4 | 4hr-120%Mg-300F | | | | | | | | | | | | | | |

| Sample | Description | Observations Comments | Shore A Hardness at Temperature (F) | | | | | | | | | | | |
|---|---|---|---|---|---|---|---|---|---|---|---|---|---|
| | | | 86 | 95 | 104 | 113 | 122 | 131 | 140 | 149 | 158 | 167 | 176 | 185 | 194 |
| F2 | 2hr-80%Mg-300F | | X | X | X | 75.0 | 70.0 | 65.0 | 50.0 | 40.0 | 30.0 | 8.0 | <5 | <5 | gooey |
| G2 | 2hr-100%Mg-300F | | | | | | | | | | | | | | |
| H2 | 2hr-120%Mg-300F | | | | | | | | | | | | | | |
| | | | | | | | | | | | | | | | |
| F4 | 4hr-80%Mg-300F | | X | X | X | 73.0 | 70.0 | 63.0 | 47.0 | 40.0 | 25.0 | 8.0 | <5 | <5 | gooey |
| G4 | 4hr-100%Mg-300F | | | | | | | | | | | | | | |
| H4 | 4hr-120%Mg-300F | | | | | | | | | | | | | | |

|  | Magox feed grade (100 mesh) | Premier Chemicals Magox feed grade (10 mesh) | Magox 93HR Block Grade | MagChem MagChem 40 |
|---|---|---|---|---|
| CaO | 5.73% | 4.03% | 3.98% | 0.75% |
| Mag | 87.97% | 91.74% | 93.27% | 98.53% |
| Mg | 53.84% | 55.8 | | |

FIG. 26

FIG. 27

PARTIAL NEUTRALIZATION OF FREE FATTY ACID MIXTURES WITH MAGNESIUM, LIVESTOCK FEED COMPOSITIONS INCLUDING THEM, AND METHODS OF MAKING SAME

RELATED APPLICATION DATA

This application claims the benefit of U.S. Patent Application Ser. No. 61/488,282, filed May 20, 2011, which is hereby incorporated herein in its entirety by reference.

TECHNICAL FIELD

The present invention relates to nutritional supplement compositions that may be used for livestock and the like, as well as to a livestock feed mixture containing them, and to their production and use.

BACKGROUND OF THE INVENTION

Methods for producing calcium soaps have been known for many years in the state of the art. Soaps are generally made from natural animal or plant fats containing triglycerides that comprise fatty acids, usually long-chain fatty acids, attached to the glycerol skeleton, which form salts by means of a process of saponification in the presence of bases.

The fatty acids that most commonly form part of these triglycerides are long-chain fatty acids such as oleic, stearic, palmitic, myristic, lauric, linoleic and linolenic acids. Fatty acids with much shorter chains also appear, such as butyric, capric, caprylic and caproic acids.

Strong inorganic alkaline metal bases, such as sodium hydroxide or potassium hydroxide, are chosen as suitable bases for the saponification reaction. In general, alkaline soaps are produced and their use is limited to cosmetics.

In the production of calcium soaps, calcium oxide (CaO) is added to the fats instead of adding alkaline metal hydroxide, which conditions the other parameters of the saponification reaction.

U.S. Pat. No. 4,642,317 discloses a process that makes it possible to increase the proportion of fat fed to ruminants, without having a deleterious effect on the rumen microorganisms, which consists of supplying the animals with fatty acids in the form of previously prepared calcium salts. One of the examples of how to produce the salts from natural fats mentions the prior saponification of the fats with sodium or potassium hydroxide, the separation of the phase containing the alkaline metal salts and the subsequent dissolution of the phase in aqueous medium and mixing it with calcium salts.

U.S. Pat. No. 4,826,694, U.S. Pat. No. 4,853,233 and U.S. Pat. No. 4,909,138 also disclose compositions for feeding ruminants wherein the main component (60-80% of the composition) is calcium or calcium salts of longer-chain fatty acids (mainly with 14 to 18 carbon atoms), although it is also mentioned that the presence of triglycerides (5%-15%) in the end product is important for the composition to be useful as feed for ruminants. The patents also disclose an apparatus and a process for producing the intended compositions, the process comprising, in this case, mixing one or more basic oxides (preferably CaO) in excess with the fatty acids and triglycerides and with water and, optionally, with an additional nutritional material as a source of proteins, thoroughly homogenizing the mixture to bring about the exothermic reaction that forms the corresponding fatty acid salts, then spreading the mixture over a flat surface so that most of the water evaporates. It is mentioned that one of the preferred embodiments of the process involves pre-heating the fatty acids, e.g. to 80 degrees C.-100 degrees C., before mixing them with the source of basic oxide, which is preferably lime (CaO).

Modifications to this basic process have subsequently been disclosed. For example, U.S. Pat. No. 5,234,701 discloses the inclusion of an aqueous solution of sodium carbonate-bicarbonate, which is a residual effluent by-product of a bicarbonate production process, as the aqueous medium for the calcium salt-forming reaction. This addition of sodium carbonate-bicarbonate seems to increase the efficiency of the process, thanks to the formation of a reaction intermediate consisting of the fatty acid sodium salt, which facilitates the formation of the corresponding calcium salt.

Other patents stress the importance of the reaction conditions to produce products with suitable characteristics when using sources of fatty acids wherein a high proportion thereof are present in the form of triglycerides. Thus, for example, U.S. Pat. No. 5,382,678 discloses the importance of mixing the source of fatty acids with the source of alkaline earth metal prior to adding water so that the end product is not a powdery solid, but takes the form of tackless free-flowing granules. It also discloses the importance of maintaining the temperature of the reaction medium at a suitable value (40 degrees C.-130 degrees C.; 110 degrees C. is used in the examples) and for a sufficient time to hydrolyze most of the glycerides that are present, releasing fatty acids that produce the desired alkaline earth metal salts.

U.S. Pat. No. 6,229,031 also highlights the importance of maintaining a suitable temperature for long enough to achieve the saponification of fatty starting materials with more than 45% triglycerides, again mentioning the need to supply the reaction mixture with additional heat as well as that generated by the exothermic reaction itself. In this case, the suitable temperature intervals mentioned are higher (90 degree C.-250 degrees C.), with higher temperatures being preferred the lower the percentage of CaO that is added, which must be between 10% and 30% of the final composition.

U.S. Pat. No. 6,576,667 and U.S. Pat. No. 6,774,252 mention that the final triglyceride content must not exceed 5% of the total composition to prevent undesired alterations during storage, suggesting that the best way to achieve sufficient saponification when using fatty materials rich in triglycerides with a high omega-3 fatty acid content is to use 2 to 3 equivalents of CaO relative to the starting material and 2 to 5 equivalents of water relative to the CaO.

U.S. Published Patent Application No. 20090220638 discloses a process of mixing the natural fats or oils with the calcium oxide, then adding water to the mixture and applying heat in a high pressure reactor. After reacting the fats and/or oils with calcium oxide, the reaction mass is allowed to cool. The calcium soap thus produced contains glycerol from the saponification of the triglycerides. No further washing, concentration (e.g. under vacuum conditions), or similar steps are necessary. The soap need only be formed using conventional techniques of extrusion into blocks, pelletization, compression, granulation, etc. This reference discloses calcium soaps with a high fatty acid content (82-86%) are directly obtained after the saponification process, and is typical of attempts to carry out saponification more effectively, and to handle purification of the saponification reaction mixture (i.e., by using significant excess calcium oxide to drive the reaction to 100% glycerol, etc.).

Other patents relating to calcium soaps in animal feed compositions include U.S. Pat. Nos. 7,318,943; 6,229,031; 5,783,714; 4,221,818; 4,198,294; 4,062,988 and 4,016,296. The foregoing references are hereby incorporated herein by reference.

Accordingly, the prior art has attempted to improve saponification processes applied to fats to maximize the amount of fatty acid salts obtained.

Typical of products currently on the market are 100% calcium soaps, such as Megalac, commercially available from Volac Limited of Royston, England. These products are 100% salts usually of palm oil or soybean oil fatty acids. Such products are generally made by saponification of triglyceride fats, usually palm oil or soybean oil, with technology that is well known. The 100% calcium soaps have a very high melt point (and actually decompose before melting) and thus cannot be prilled effectively.

Beyond the problems of creating magnesium salts of fatty acids of sufficient nutritive value and digestibility (i.e., relatively high salt/free acid ratio, especially for ruminants), another set of concomitant problems are associated with the transportation and use of nutritional supplements of this sort related to their transport, storage, handling and dispensing, and use in processing. One of the problems associated with free fatty acid mixtures (100% non-salted) is that they tend to have relatively low onset melting points such that they may melt when exposed to elevated ambient temperature, such as when stored in silos, packaged in bags, subjected to the heat associated with processing or milling the material with base particulate feeds, or otherwise transporting the material in warmer weather or warm climates.

The relatively low onset melting points also adversely affect handling and dispensing, as it more preferable to handle and dispense materials, both as a consumer and in industrial processing, that flow as a relatively dry, non-tacky particulate.

Another related problem is that the 100% free fatty acid products are subject to caking and agglomeration upon being subjected to pressure, whether as a result of storage in silos, packing and transport in bags, etc.

Likewise, where it is desired to blend or mill such nutritional supplements so as to produce particulate livestock feed blends, current free fatty acid products are subject to melting or liquefaction during processing, making them unsuitable for this type of industrial processing of this type. In this regard, while 100% salt products do have acceptable bulk handling properties and can be pelleted, they cannot be prilled. The 100% calcium salted fatty acid products typically are all made from palm oil or soybean oil and with the higher unsaturated fatty acid level, these products have a negative nutritional effect on the rumen relative to the more saturated free fatty acid mixtures like Energy Booster 100 (EB 100), commercially available from Milk Specialties Global Animal Nutrition of Eden Prairie, Wis.

Accordingly, there remains a need for nutritional supplements comprising fatty acid mixtures or magnesium salts of fatty acids that feature the required nutritive value and digestibility, yet are improved with respect to properties that are important to the transportation, storage, handling and industrial processing applied in the particulate livestock feed blends.

SUMMARY OF THE INVENTION

The present invention includes a nutritional supplement composition that may be used for livestock and the like, as well as to a livestock feed mixture containing same. Also included are methods of preparing the nutritional supplement composition, the livestock feed mixture, as well as methods of providing nutrition to livestock and the like.

The present invention includes a method of partially salting (magnesifying/neutralizing) free fatty acids such that they can be prilled or flaked, exhibit improved compaction in bulk storage, improved flow and handling properties (flow from bulk bins, through augers, etc.), and can be processed through traditional feed pelleting mills to make a pelleted feed.

Although not limited to the theory of the invention, it is believed these improved properties are a result of increased onset melt point and hardness vs. temperature, as compared to mixture of free fatty acids.

The preparation of 100% salts of fatty acids is well known and these materials are typically prepared by well established processes of saponification of triglyceride fats and oils.

In contrast to prior art methods, it is preferred that the process of the present invention starts with free fatty acids rather than triglycerides, and produces directly a partially salted (magnesified, i.e., neutralized with magnesium) magnesium salt of the starting fatty acid mixture, that is, the preferred starting material consists essentially of a fatty acid or fatty acid mixture. By simply neutralizing a mixture of free fatty acids with, for instance, magnesium oxide (i.e., no triglycerides present, no excess magnesium oxide, and no glycerol produced (which then has to be separated)), the product of the present invention avoids these disadvantages associated with products made from fats directly. The process of the present invention may also start with fats with the purification of the fatty acids prior to further partial salting.

The free fatty acid products (like EB 100) have problematic flow problems, and thus cannot be handled or used in bulk, and cannot be pelleted.

The 100% salt products do have good bulk handling properties and can be pelleted but they cannot be prilled. The 100% calcium salted fatty acid products are all made from palm oil or soybean oil and with the higher unsaturated fatty acid level, these products have a negative nutritional effect on the rumen relative to the more saturated free fatty acid mixtures like EB 100.

As a result of the process of the present invention, one may produce a partial magnesium salt of fatty acid mixtures, i.e., from fatty acid mixtures such as those exemplified by EB100 fatty acid mixtures, and thereby produce products that have the best properties of both state of the art technologies, i.e., EB100 free fatty acids and Megalac 100% calcium salts of palm oil fatty acids.

The partially salted fatty acid mixture of the present invention may be prilled or flaked, in accordance with methods known and used in the art.

The preferred fatty acid made and used in the present invention is a mixture of tallow-free fatty acids and the magnesium salts of tallow fatty acids, although the invention may be produced or practiced using any fatty acid mixture, although with other mixtures, one may have to use higher percent magnesium for lower melting/softer mixtures. It is also preferred that the free fatty acids used in accordance with the present invention include those having a degree of unsaturation such that the iodine number is less than 20, most preferably less than 10.

Magnesium may be incorporated in any form adapted to form the salt(s) of the fatty acid(s), as is known in the art, such as in the form of magnesium oxide or magnesium hydroxide, broadly in an amount equivalent to about 15% to about 75%, and preferably in an amount equivalent to about 25% to about 55% based upon the theoretical requirement to accomplish the total neutralization of all of fatty acid present; i.e., in the range of from about 25 to about 55% of the total moles of the tallow fatty acid(s), such that they are converted (neutralized) to their magnesium salts.

The melt point and hardness are believed to be a function of the percent of magnesium salting (i.e., percent neutralization). It is preferred that the onset melt point is about 170 F, although commercially important improved properties for handling, flow and pelleting can be obtained at melt points below 170 (though a melt point of 120-130 F such as that of commercially available EB100 is too low), and that the temperature for hardness of 15 Shore A units is about 170 F. A Shore A hardness less than 15 at 170 F (e.g. Shore A of 5-10 at 170 F) or a Shore A hardness of 15 at a lesser temp than 170 F (e.g. Shore A of 15 at say 150 F) likely will yield good commercially important improved properties, though it is known that the properties of free fatty acid mixtures like commercially available EB100 or its competitors do not have sufficient Shore A hardness at 100-120 F to demonstrate improved properties for handling, flow and pelleting.

In contrast with current products, some of the novel properties and uses of the fatty acid mixtures of the present invention include that it may be stored, transported and used in bulk (without compaction or disadvantageous liquefaction), while comparative products, such as EB 100 (and other similar mixtures of free fatty acids from tallow, palm or soy) cannot.

As one measure of the compressibility of the fatty acid mixtures of the present invention, a 50-100 gram/weight at 50 degrees centigrade for 1 hour (about 2 psi-4 psi) did not result in compaction sufficient to restrict the ability of the flaked or prilled product to be poured (which conditions brought about compaction of EB 100).

One aspect of the present invention is drawn to a feed supplement for increasing the fat intake level of animals, including animal feed and the fatty acid mixture of the present invention. The animal feed typically may be a dry feed.

The fatty acid mixtures of the present invention may be used for pelleted feed applications while comparative products, such as EB 100 and other similar mixtures of free fatty acids from tallow, palm or soy, cannot be pelleted.

The fatty acid mixtures of the present invention may stored, transported and used in dairies in hot climates (e.g., Florida, Arizona and New Mexico) while comparative products, such as EB 100 (and other similar mixtures of free fatty acids from tallow, palm or soy) cannot be handled in these climates without adverse effects on their physical form.

The fatty acid mixtures of the present invention also feature controllable, increased onset melt point and controllable, increased hardness at all temperatures relative to free fatty acid mixtures. The present invention thus offers a method by which the onset melt point can be controlled and varied.

While a 100% calcium salt of a free fatty acid mixture of oils like palm oil and soy (which are liquid at room temperature) not only produces a solid product but one that has good flow properties and can be pelleted, it is also well known that the unsaturated fatty acids present in palm and soy have a negative effect on the rumen which limits the dose that can be fed to dairy cattle.

It is also well known that mixtures of tallow fatty acids (with the lower degree of saturation compared to palm oil and soy are solids at ambient temperature), can be prilled, but do not have good flow properties and cannot be pelleted. It is also well known that tallow fatty acids, owing to their low level of unsaturation, do not have a negative impact on the rumen exhibited in the palm oil and soy fatty acid blends.

As to the increased onset melt point, a partially salted magnesium salt of a fatty acid mixture is a complex mixture of lower melting fatty acids and non-melting magnesium salts. Accordingly, these partially neutralized magnesium fatty acid mixtures would likely not exhibit an increase in onset melt point since the non-salted fatty acids would melt at their normal melt point and the magnesium salts would just be suspended in the matrix of fatty acids. By virtue of the present invention, and while not limited to the theory by which it operates or achieves beneficial results, it has been discovered that, by mechanisms not fully understood, the magnesium salts of a fraction of the free fatty acids present seem to complex with the remaining free fatty acids to form a mixture that has an increased onset melt point. This increase in melt point was discovered to be positive and non-linear with increasing percent magnesium.

With respect to the hardness versus temperature, by the same rationale as for increased onset melt point, it was not anticipated that the partial salted magnesium fatty acids would exhibit such an improved hardness relative to the free fatty acids. What was discovered was that by increasing the degree of salting by increasing the percent of magnesium salts of the fatty acids present that, by mechanisms not fully understood, the magnesium salts of a fraction of the free fatty acids present, seem to complex with the remaining free fatty acids to form a mixture which is harder (as measured by Shore A) at any given temperature up to the melt point relative to free fatty acid mixtures. This increase as with onset melt point is also non-linear.

The product of the present invention compares favorably to prior art formulations, such as that represented by Energy Booster 100 (EB100) commercially available from Milk Specialties Global Animal Nutrition of Eden Prairie, Wisconsin. The EB100 is a prilled product, but may be made and sold as a flaked product. Prilling is a spray chilling process wherein the liquid fatty acid mixture is sprayed at the top of a tall tower into a chilled air stream forming very small spheres. The EB100 is a mixture of tallow free fatty acids (from animal fat), and features an onset Melt Point ≤130 F and a temperature for Hardness of 15 Shore A units at 120 F. It may be used as an energy source for high producing dairy cows. The problems associated with this product include that it cannot be used in bulk applications (super sacks, bins, silos, trucks, etc.) due to compression into blocks, chunks, bridging, etc. In addition, it cannot be used for pelleted feed applications as pellet mash is at 160-165 degrees F. and then is heated higher through the dies, because EB100 melts at 130 degrees F. and thus binds the augers, sticks to the mash tank, and forms a soft pellet. It cannot be used conveniently on dairies in hot climates (e.g., Florida, Arizona and New Mexico) owing to its susceptibility to surface melting and resultant compaction.

In general terms, the invention thus includes a method of producing a partially magnesium/neutralizing free fatty acid mixture, a partially magnesium-salted free fatty acid mixture, a livestock feed mixture containing a partially magnesium/neutralized free fatty acid mixture, a method of producing a livestock feed mixture containing a partially magnesium/neutralized free fatty acid mixture, a method of providing nutrition to livestock by feeding a mixture containing a partially magnesium/neutralized free fatty acid mixture, and a method of providing nutrition to livestock by feeding a mixture containing a partially magnesium/neutralized free fatty acid mixture.

The method of producing a partially magnesium/neutralized free fatty acid mixture comprises the steps of: (a) preparing a mixture of: (i) an amount of a free fatty acid; and (ii) an amount of a magnesium-containing material comprising a magnesium-containing basic compound adapted to form a magnesium salt of the fatty acid, the magnesium-containing material being present in an amount in the range of from about 25% to about 55% of the amount of a free fatty acid based upon the theoretical requirement to accomplish the total neutralization of all of fatty acid present; and (b) maintaining the mixture at sufficient temperature and for sufficient amount of time so as to form a mixture of free fatty acid and magnesium/ neutralized free fatty acid. It will be appreciated that the mixture of free fatty acid and magnesium/neutralized free fatty acid may be obtained either by mixing the already salted fatty acid with free fatty acid in a melt to obtain the desired ratio, or by proceeding from a free fatty acid (or mixture thereof) and subjecting it to a partially salting reaction to obtain the desired ratio.

The free fatty acid may be selected from the group consisting of tallow and non-tallow fatty acids, and mixtures thereof, and the non-tallow fatty acids may be selected from the group consisting of fatty acids from palm oil, soy oil, fish oil, linseed oil and flax oil, and mixtures thereof.

It is preferred that the reaction mixture is maintained at a temperature in the range of from about 240 degrees to about 300 degrees Fahrenheit during step (b).

The mixture may be additionally subjected to a prilling process or a flaking process, depending upon the desired product logistics parameters (storage, transport, etc.) and application.

The partially magnesium/neutralized free fatty acid mixture of the present invention generally includes a composition comprising, and preferably consisting essentially of, a solid particulate mixture of free fatty acid and a magnesium salt of a fatty acid, the magnesium salt of a fatty acid being present in an amount in the range of from about 25% to about 55% of the amount of the free fatty acid based upon the theoretical requirement to accomplish the total neutralization of all of fatty acid present.

It is preferred that the free fatty acid comprises tallow fatty acid, and that the magnesium salt of a fatty acid comprises a magnesium salt of a tallow fatty acid, although the free fatty acid may be selected from the group consisting of tallow and non-tallow fatty acids, and mixtures thereof. The non-tallow fatty acids may be selected from the group consisting of fatty acids from palm oil, soy oil, fish oil, linseed oil and flax oil, and mixtures thereof.

It is preferred that the mixture is a solid having an onset melt point of at least 170 degrees Fahrenheit, and that it have a hardness of at least about 15 shore A units at 170 degrees Fahrenheit, although one may adjust the properties slightly with a range of a hardness of lesser Shore A than 15 at 170 F (e.g. Shore A of 5-10 at 170 F, more preferably 10-15 at 170 F) or a Shore A hardness of 15 at a lesser temp than 170 F (e.g. Shore A of 15 at 140-170, such as Shore A of 15 at 150 F) while maintaining the desired beneficial properties. Most preferably, the mixture is a solid having an onset melt point of at least 170 degrees Fahrenheit, and a hardness of up to 15 Shore A units (typically from about 5 to about 15 units) at 170 degrees Fahrenheit.

The invention also includes a livestock feed mixture containing a partially magnesium/neutralized free fatty acid mixture, the livestock feed composition comprises, and preferably consists essentially of: (a) a solid particulate livestock feed material and (b) a solidified particulate mixture of (i) free fatty acid and (ii) a magnesium salt of a fatty acid (as described herein), the magnesium salt of a fatty acid being present in an amount in the range of from about 25% to about 55% of the amount of the free fatty acid based upon the theoretical requirement to accomplish the total neutralization of all of fatty acid present.

The invention also includes a method of producing a livestock feed composition containing partially magnesium/neutralized free fatty acid mixture, comprising the steps of: (a) preparing a blend of: (i) a solid particulate livestock feed material and (ii) a solid particulate mixture of free fatty acid and a magnesium salt of a fatty acid (as described herein), the magnesium salt of a fatty acid being present in an amount in the range of from about 25% to about 55% of the amount of the free fatty acid based upon the theoretical requirement to accomplish the total neutralization of all of fatty acid present, so as to obtain a solid particulate livestock feed composition; and (b) rendering the blend into a solid particulate livestock feed composition.

The partially magnesium/neutralized free fatty acid mixture may be produced by a prilling process or a flaking process.

The solid particulate livestock feed composition preferably is rendered into pellets, although other physical forms may be used.

The present invention further includes a method of providing nutrition to livestock by feeding a mixture containing a partially magnesium/neutralized free fatty acid mixture, the method comprising administering to a livestock animal a solid particulate livestock feed composition comprising: (a) a solid particulate livestock feed material; and (b) a solid particulate mixture of free fatty acid and a magnesium salt of a fatty acid (as described herein), the magnesium salt of a fatty acid being present in an amount in the range of from about 25% to about 55% of the amount of the free fatty acid based upon the theoretical requirement to accomplish the total neutralization of all of fatty acid present.

The solid particulate livestock feed composition preferably is in pellet form, and typically will be administered in nutritionally effective amounts in accordance with livestock care and nutrition practices known in the art.

The present invention also represents a variation upon the calcium-containing formulations and methods described in U.S. Provisional Patent Application Ser. No. 61/280,346, filed Nov. 2, 2009, and U.S. patent application Ser. No. 12/755,800 filed Apr. 7, 2010, which are hereby incorporated in their entirety herein by reference. The formulations and methods of the present invention may be used in conjunction with those calcium-containing formulations and methods. Both calcium-containing formulations and magnesium-containing formulations may be blended or otherwise used in conjunction with one another as desired.

BRIEF DESCRIPTION OF THE DRAWINGS

FIG. 9 is a laboratory notebook record of acid value analysis.

FIG. 10 is a laboratory notebook record of melting point and hardness profile analysis for an exemplary formulation.

FIG. 11 is a laboratory notebook record of melting point analysis for the exemplary formulation.

FIG. 12 is a laboratory notebook record of Shore A Hardness analysis for the exemplary formulation.

Figure 15:
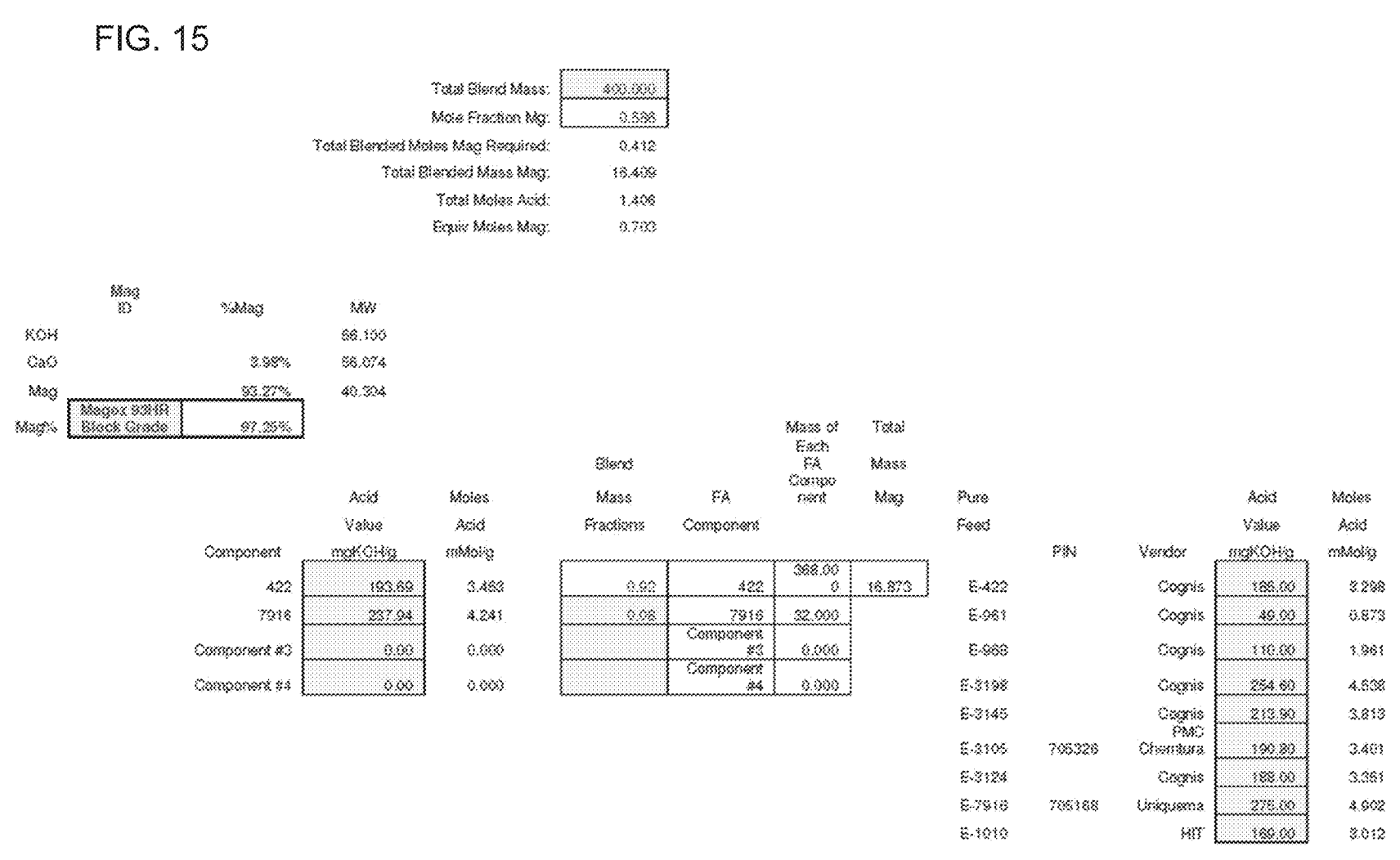

FIG. 15 is a laboratory notebook record of a production trial for the exemplary formulation.

Figure 16:
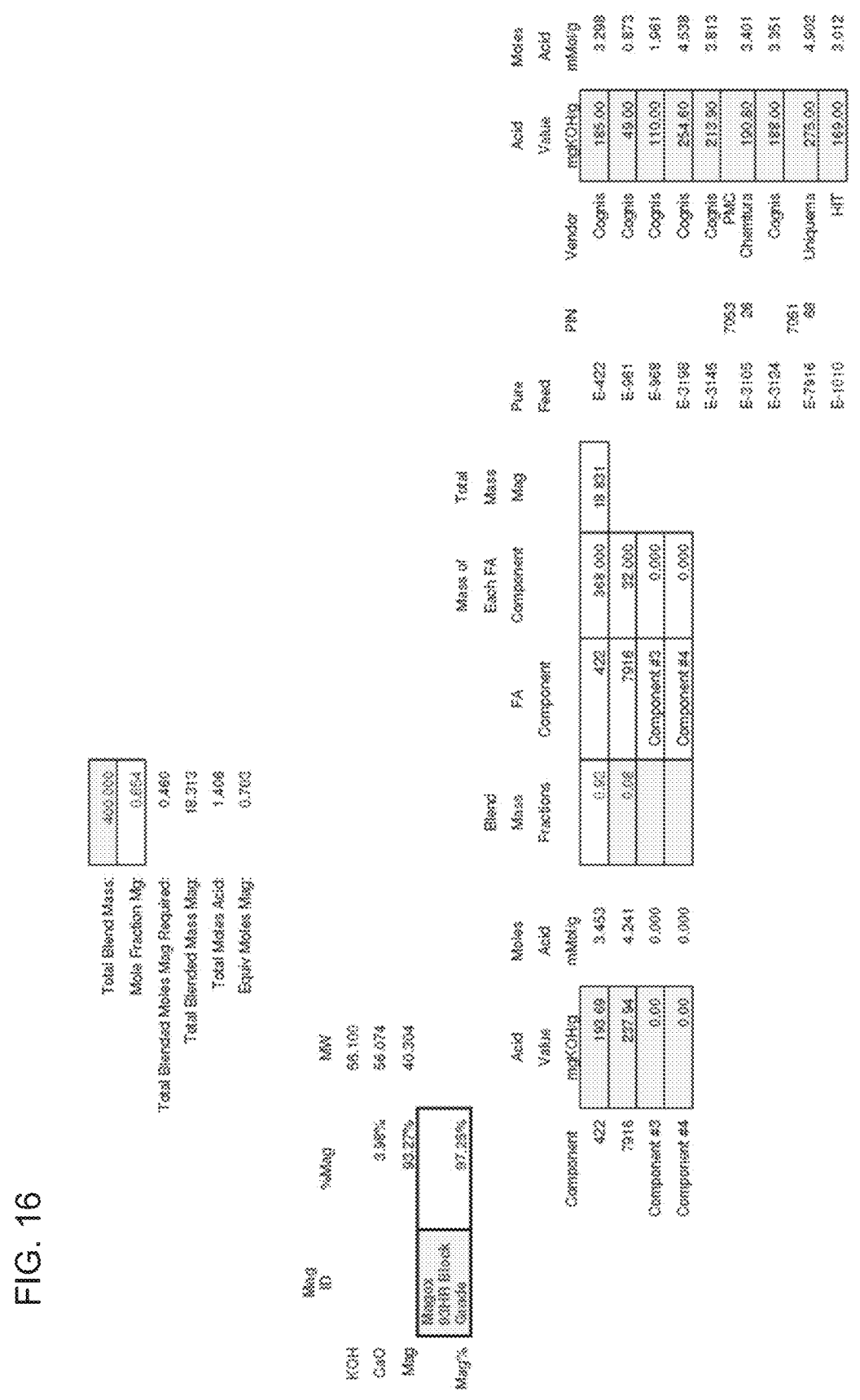

FIG. 16 is a laboratory notebook record of a production trial for the exemplary formulation.

FIG. 17 is a summary of commercially available constituent materials for production of the exemplary formulation.

FIG. 18 is a laboratory notebook record of acid value analysis for an alternative exemplary formulation.

Figure 19:
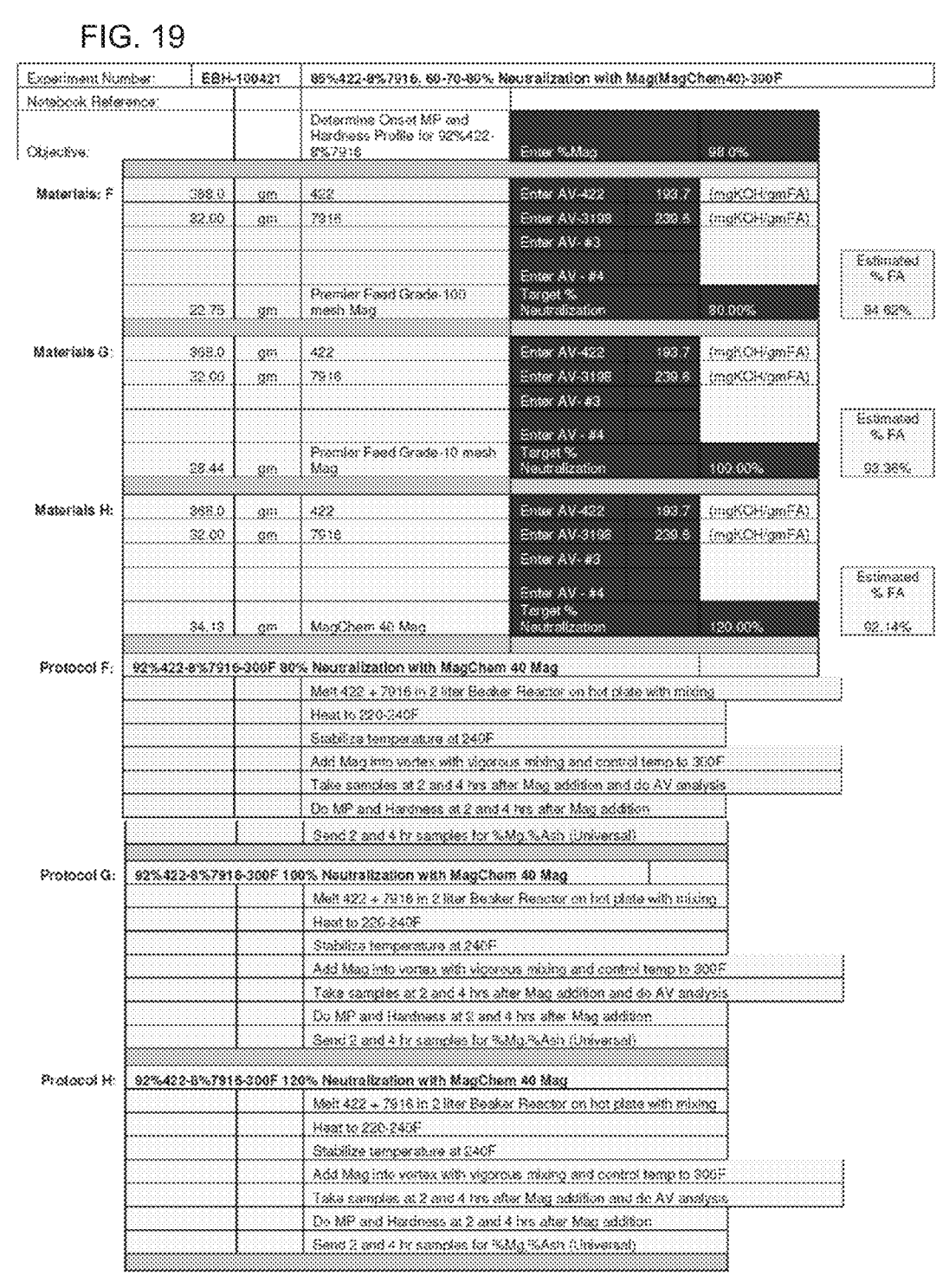

FIG. 19 is a laboratory notebook record of melting point and hardness profile analysis for the alternative exemplary formulation.

FIG. 20 is a laboratory notebook record of melting point analysis for the alternative exemplary formulation.

FIG. 21 is a laboratory notebook record of Shore A Hardness analysis for the alternative exemplary formulation.

Figure 22:
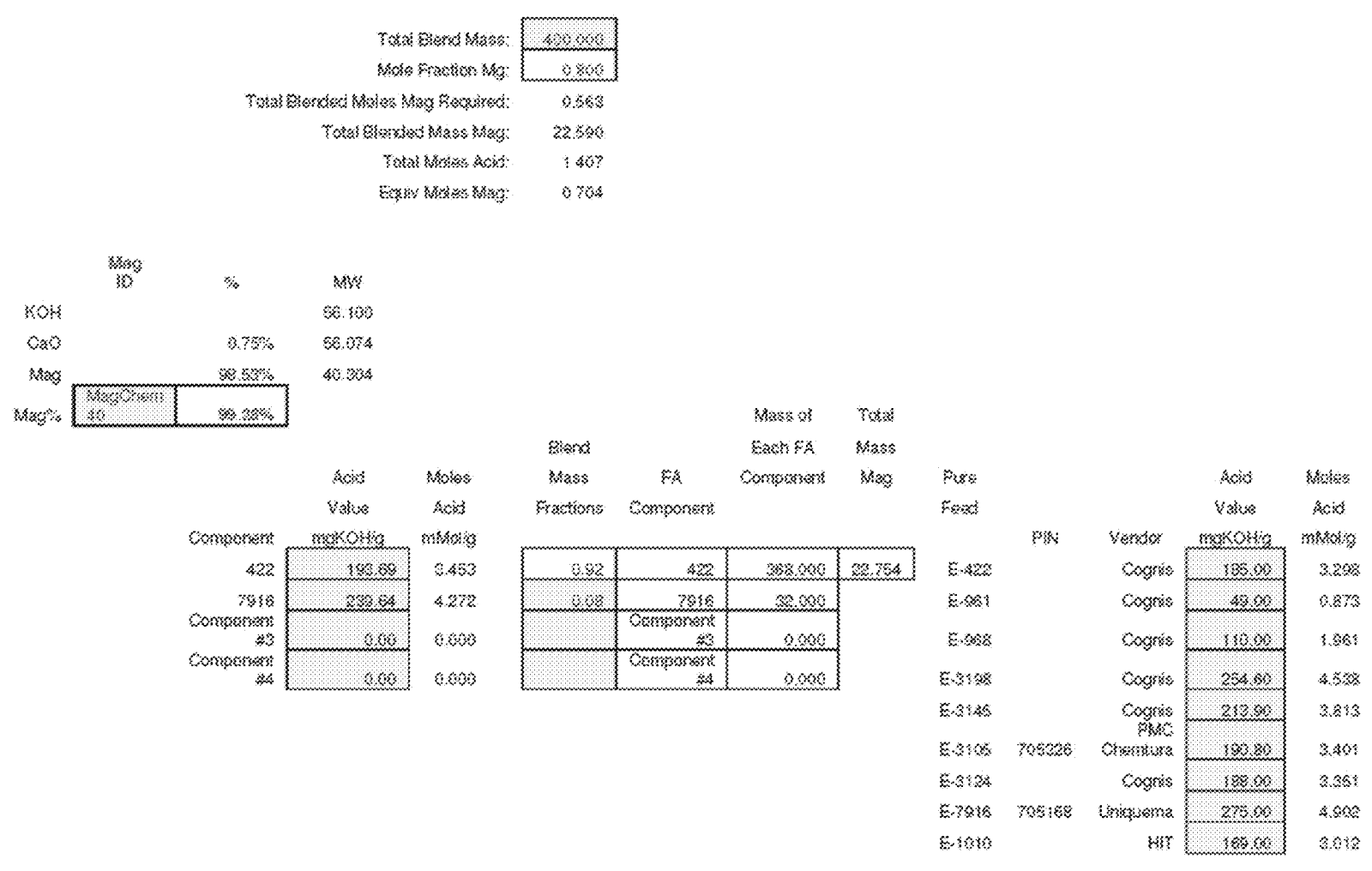

FIG. 22 is a laboratory notebook record of a production run for the alternative exemplary formulation.

Figure 23:
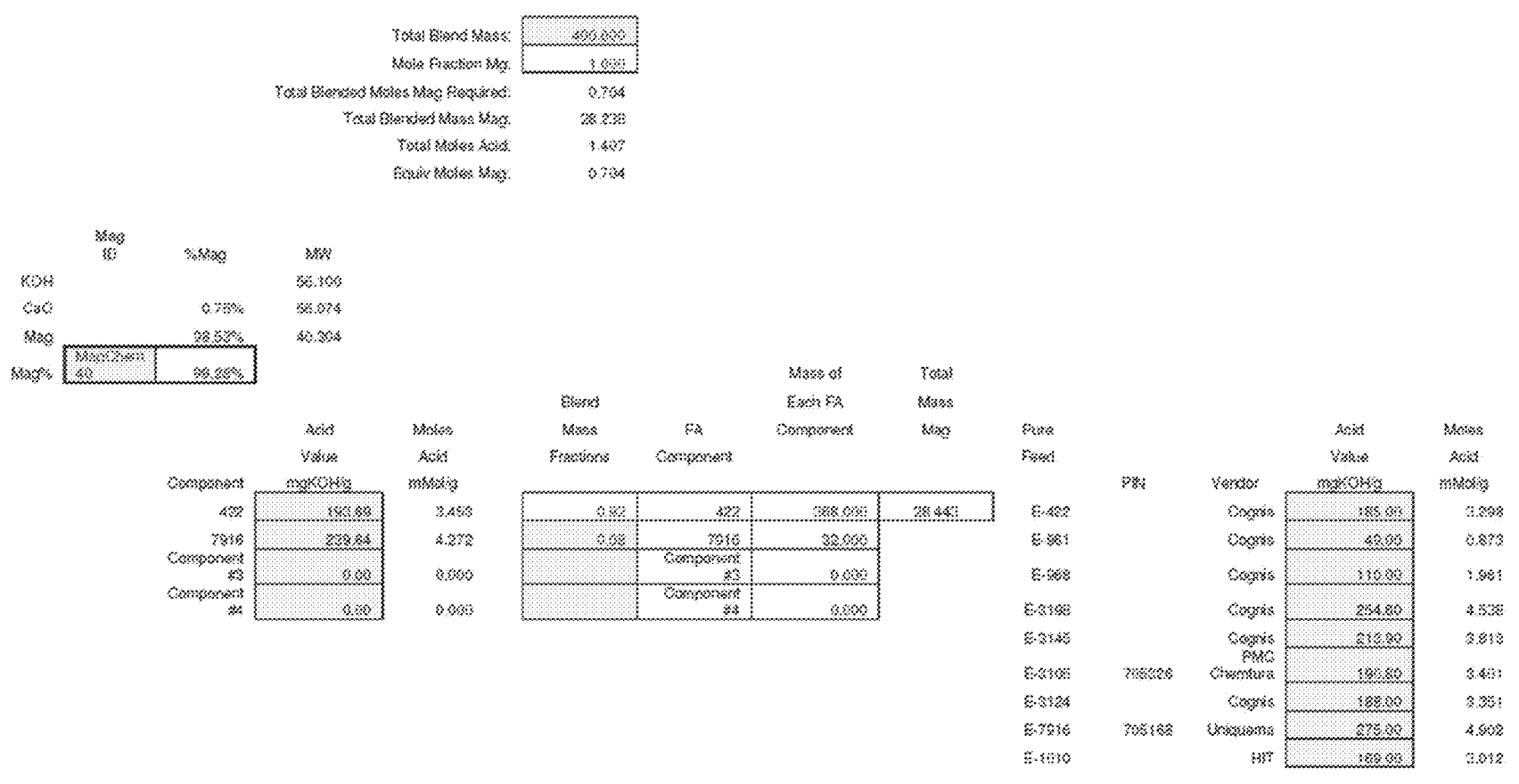

FIG. 23 is a laboratory notebook record of a production run for the alternative exemplary formulation.

Figure 24:
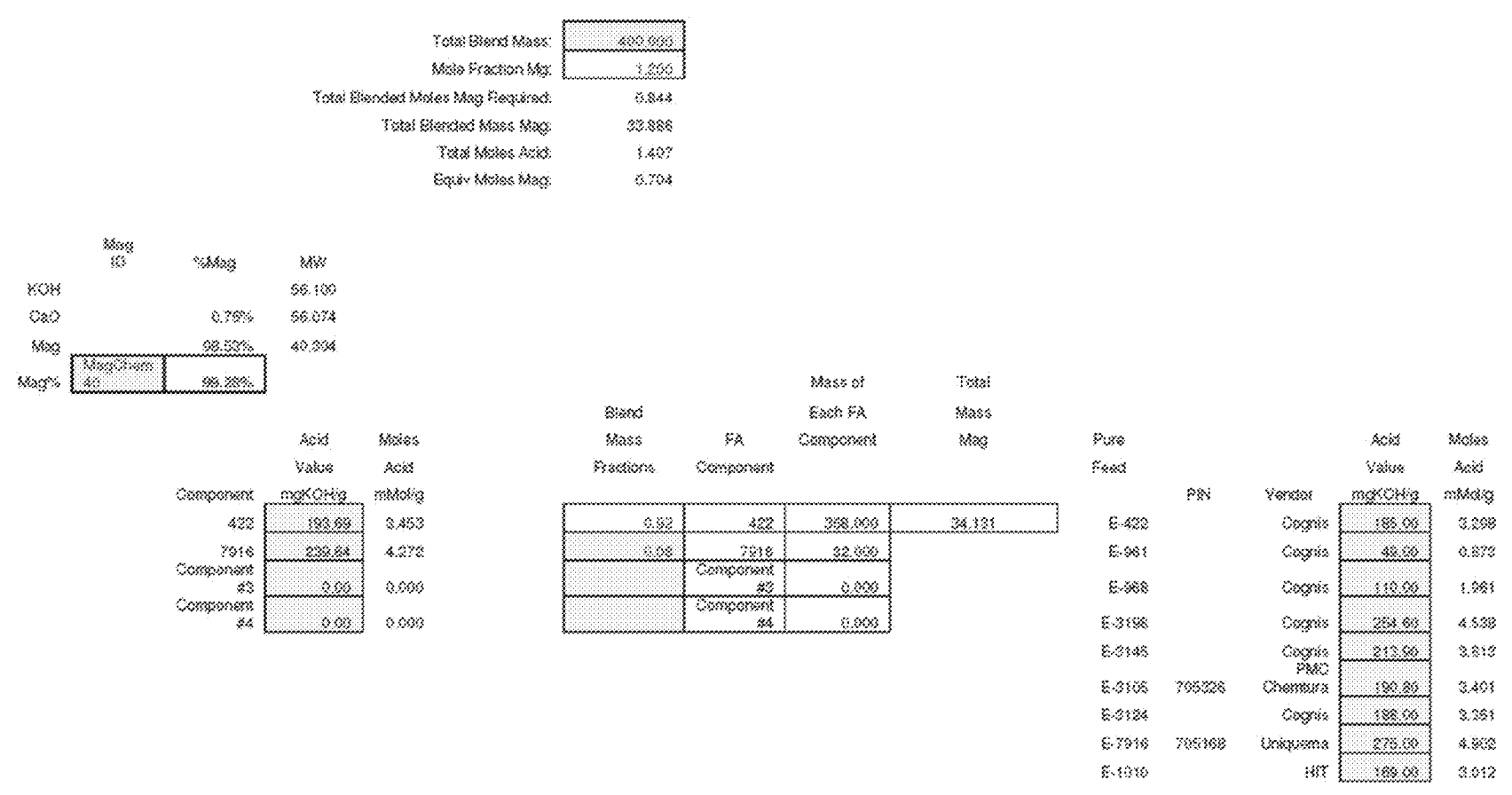

FIG. 24 is a laboratory notebook record of a production run for the alternative exemplary formulation.

FIG. 25 is a summary of the commercially available constituent materials for production of the alternative exemplary formulation.

FIG. 26 is data relating to raw materials and processing aids.

FIG. 27 is data relating to raw materials and processing aids.

DETAILED DESCRIPTION OF THE PREFERRED EMBODIMENTS

Figure 1:
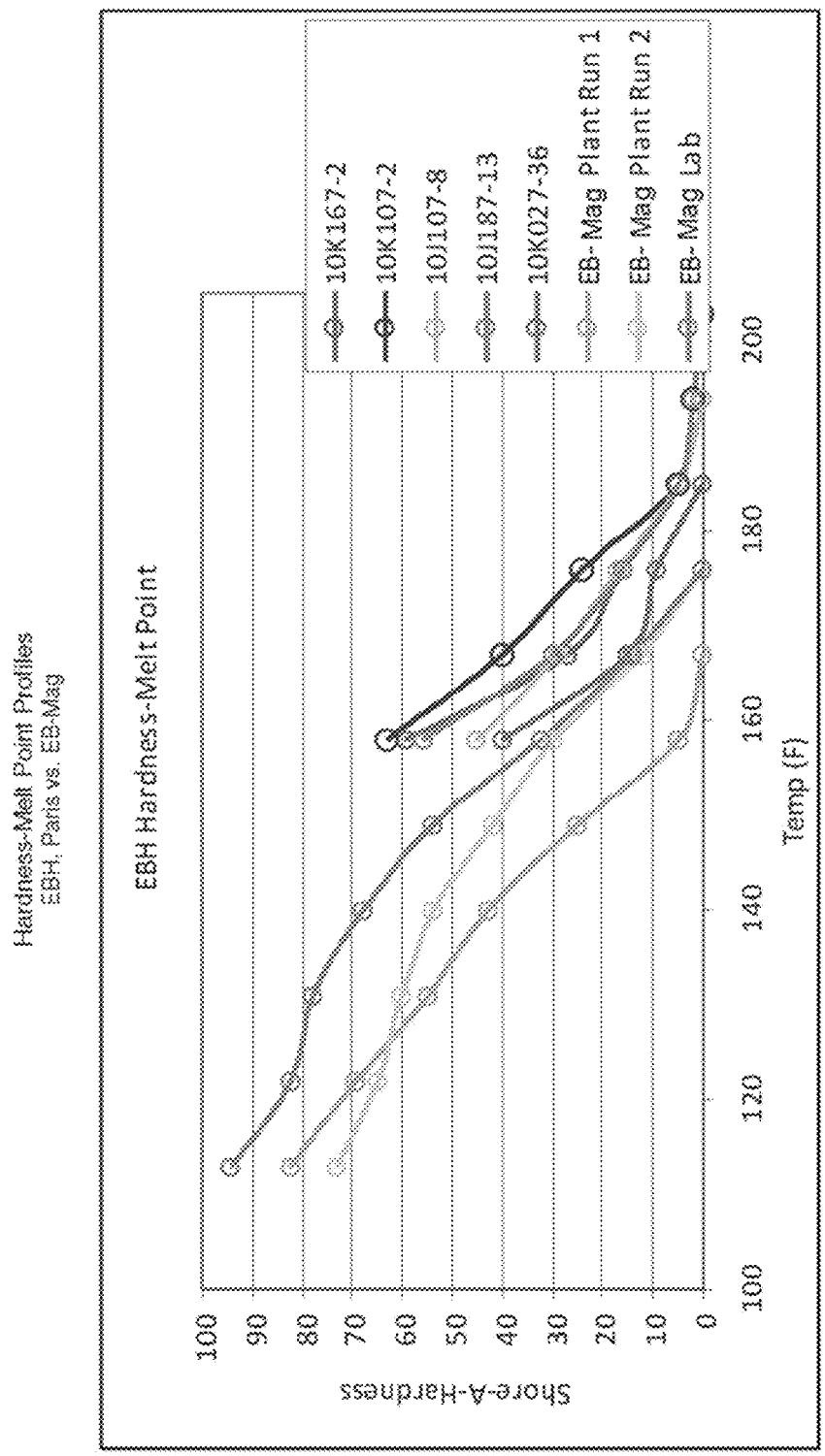
FIG. 1 is a graph showing a comparison of Hardness-Melt Point Profiles of EBH, Paris vs. EB-Mag in accordance with one embodiment of the present invention.

In accordance with the foregoing summary of the invention, the following presents a detailed description of the preferred embodiments, which are considered to be the best mode thereof.

The preferred method and compositions described herein are not intended to be exhaustive or to limit the invention to the precise forms disclosed. They are chosen and described to explain the principles of the invention and the application of the method to practical uses so that others skilled in the art may practice the invention.

As a preferred but non-limiting example of the method by which compositions of the present invention may be made, the following steps may be followed:

1. Heat mixture of free fatty acids to 255-270 degrees F.
2. Add desired neutralization equivalents of magnesium as magnesium oxide or magnesium hydroxide with good mixing. The exothermic reaction of magnesium oxide or hydroxide with free fatty acids causes temperature to rise to within a range of about 255-300 degrees F. (dependent on insulation and heat loss of reactor system).
3. Hold reaction mixture at 255-300 degrees F. until reaction is complete as measured by change in Acid Value (AV). The reaction may be monitored by determining Acid Value (AV) of the material; for example: for a target of 40% magnesium/neutralization the AV at completion would be about 60% of the starting AV (i.e., AV final=0.6*AV starting).
4. When reaction is complete as determined in 3 above, material is either prilled in a prilling (spray chilling) tower or flaked on a rotary drum flaker by use of methods and apparatus well known in the field.

Normally, the maximum percentage of fat attainable for the 100% magnesium soaps or the prior art is about 80-82% due to the 100% magnesium level while the maximum percentage of fat attainable is over 90 percent fat for products made in accordance with the present invention.

While the 100% calcium soap products do not melt, the melt point and hardness can be controlled for the partially magnesium/neutralized products made in accordance with the present invention.

The corresponding calcium soaps have historically been made from palm oil and soybean oil. Both these oils and free fatty acid mixtures from these oils are liquids at room temperature and so to sell these products as a solid into the dairy industry the companies using these starting materials had to make the calcium soaps.

Example of the Manufacturing Process of the Present Invention

A repeatable, controlled process was developed for partial magnesium/neutralization of free fatty acids which included heating melted free fatty acids to 255-270 F slowly adding the calculated amount of magnesium oxide and allowing the reaction to proceed for approximately 2 hours after all magnesium oxide was added, and, after the final addition of magnesium oxide, typically remains in the range of 255-300 F throughout the 2 hour reaction.

As an alternative to a timed reaction, the initial Acid Value (AV) can be obtained by known titration methods and the AV monitored throughout the reaction until AV value levels out (e.g. initial AV=185; for 40% magnesium/neutralization final AV=111).

Examples of two production trials and data taken therefrom are set forth in FIGS. 9-17 and FIGS. 18-25 respectively. This data relates specific exemplary formulations and AV analysis, melting point onset and hardness profile, neutralization data and physical observations, Shore A Hardness at temperature, individual formulations and their commercially available constituent materials.

Melt Point and Hardness of EBH

Hardness and melt point onset data of various prilled fat products were compared in a series of trials as follows:

BACKGROUND

Energy Booster Hard (EBH) is a prilled fat blend containing a minimum of 90% total fatty acids and minimum calcium of 2.5% with a guaranteed melt point of 170 F. To prepare a product that may be used in the prilled fat market, a Energy Booster Mag (EB-Mag) with a target melt point of 170 F for improved handling was developed in accordance with the present invention. It contains a minimum total fatty acids of 90.0%; Unsaponifiable matter 6.0% max; and 1.5% minimum magnesium. To assess EB-Mag handling, pelleting and mixing, a data set of melt point and hardness was established.

This experimental data was gathered on the melt point and hardness of finished product prilled fats to assess EB-Mag performance.

Materials and Methods

Materials: EBH prilled fats from Boscobel, Wis. and Paris, Ill. plants; Hot plate and Oven.

Method
1. Melt prilled fats in an aluminum moisture pan on hot plate until sample becomes a uniform liquid (do not overheat).
2. Once completely melted, cool container in chilled ethanol/water mixture until solidified.
3. Place sample "puck" upside down in pan to expose smooth side for testing with Shore-A-Hardness Durometer.
4. Break off small sample wedge from "puck" and place on filter pad in another pan. This sample will be used to determine melt point.
5. Place samples in oven and let temperature reach 45 C. Once temperature is at 45 C set timer for 15 minutes.
6. Remove sample from oven and check hardness. Place back in oven.
7. Increase temperature to 50 C and set timer for 15 min once temp reached.
8. Keep increasing temp at 5 C increments at 15 minute intervals until sample hardness is <5 or filter pad sample melts.
9. Record results and observations.

Figures 26, 27:
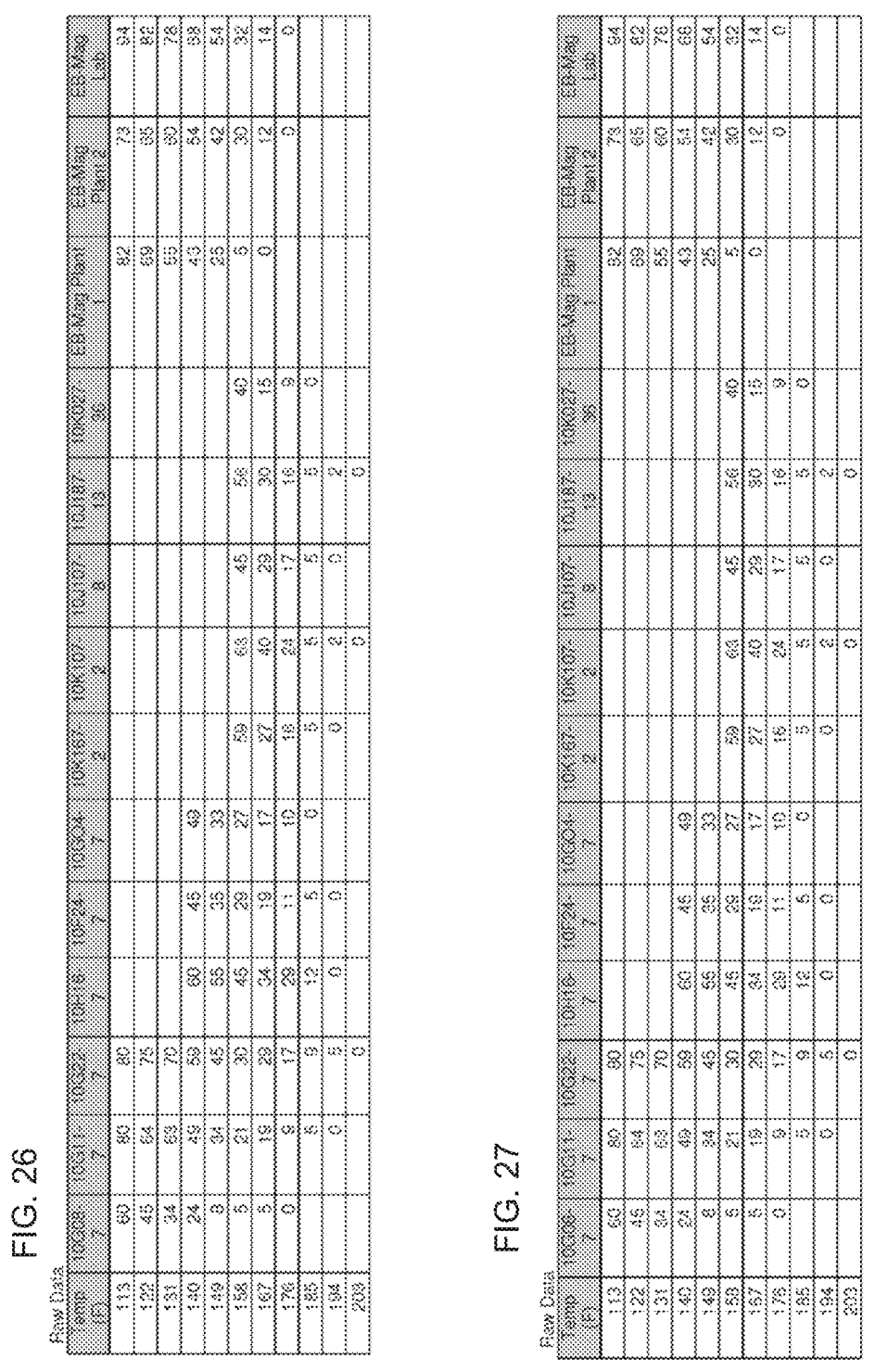

FIGS. 26 and 27 set forth the raw data obtained on several formulation trials.

Figure 2:
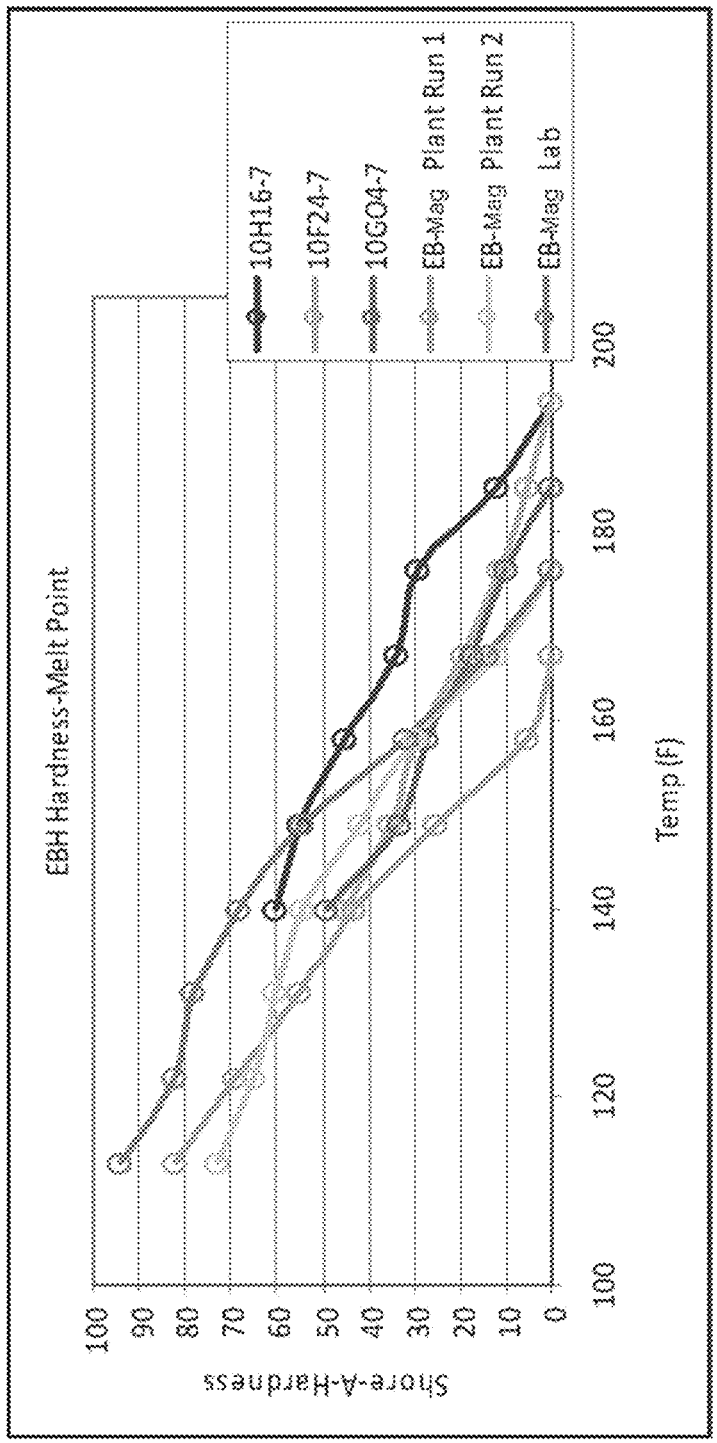
FIG. 2 is a graph showing a comparison of Hardness-Melt Point Profiles of EBH, Boscobel vs. EB-Mag in accordance with one embodiment of the present invention.
Figure 3:
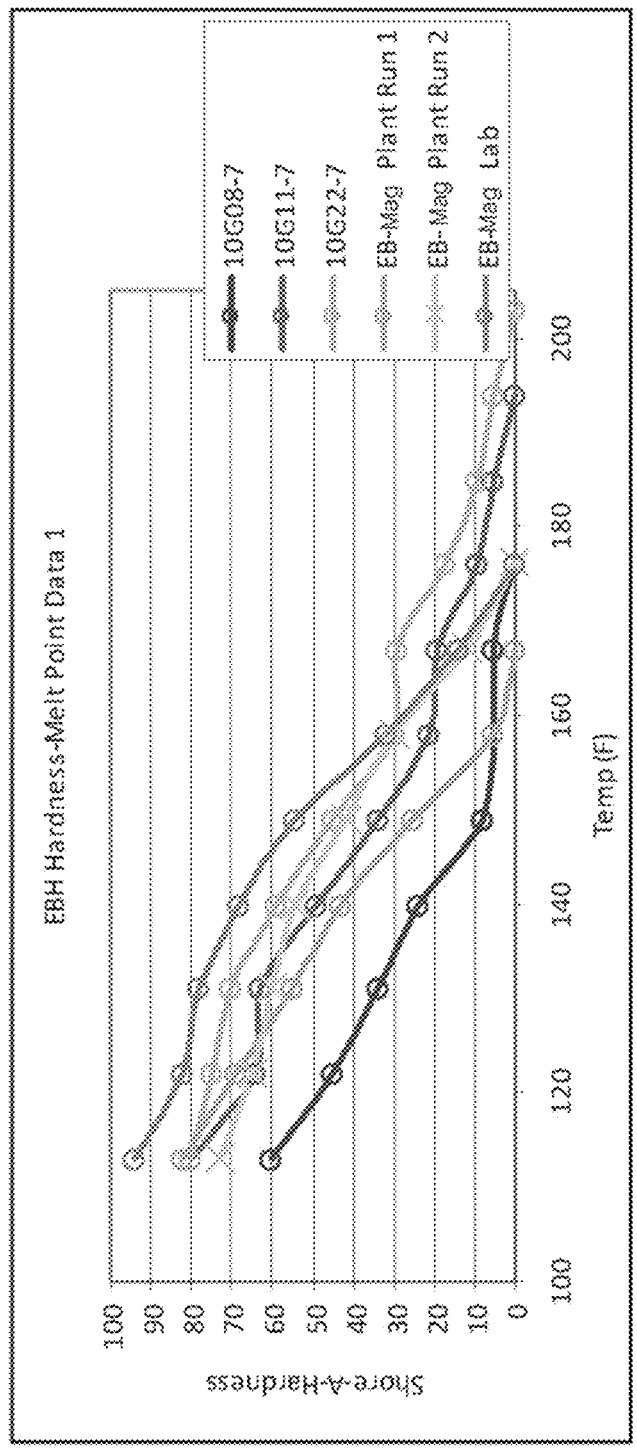
FIG. 3 is a graph showing a comparison of Hardness-Melt Point Data for EBH formulations in accordance with one embodiment of the present invention.

FIG. 1 is a graph showing a comparison of Hardness-Melt Point Profiles of EBH, Paris vs. EB-Mag in accordance with one embodiment of the present invention;

FIG. 2 is a graph showing a comparison of Hardness-Melt Point Profiles of EBH, Boscobel vs. EB-Mag in accordance with one embodiment of the present invention. FIG. 3 is a graph showing a comparison of Hardness-Melt Point Data for EBH formulations in accordance with one embodiment of the present invention.

Figure 4:
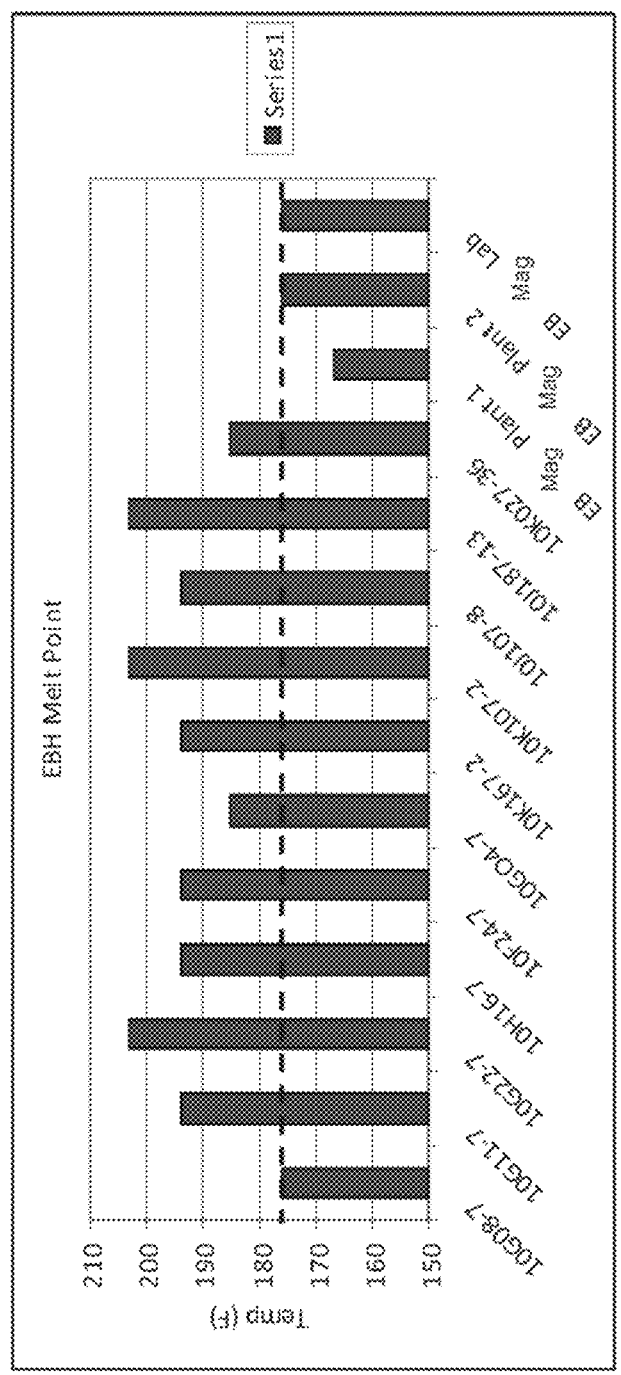
FIG. 4 is a graph showing a comparison of EBH Melt Point Data for EBH formulations in accordance with one embodiment of the present invention.

FIG. 4 is a graph showing a comparison of EBH Melt Point Data for EBH formulations in accordance with one embodiment of the present invention.

Hardness Characteristics

Figure 5:
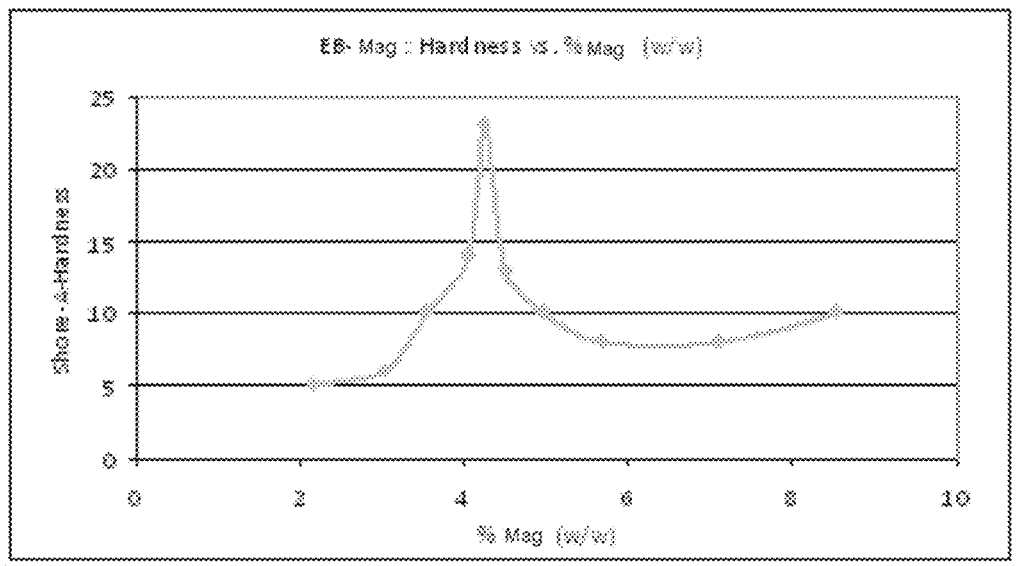
FIG. 5 is a graph of Shore A hardness versus magnesium oxide content for multiple percentages of magnesium, in accordance with one embodiment of the present invention.

FIG. 5 is a graph of Shore A hardness versus magnesium oxide content for multiple percentages of magnesium, in accordance with one embodiment of the present invention, based upon the following raw data:

| Raw Data | |
|---|---|
| % Mag | Hardness |
| 2.17 | 5 |
| 3.04 | 6 |
| 3.54 | 10 |
| 4.05 | 14 |
| 4.27 | 23 |
| 4.5 | 13 |
| 4.98 | 10 |
| 5.69 | 8 |
| 7.11 | 8 |
| 8.53 | 10 |

The data presented in FIG. 5 demonstrates that the hardness of the product in support of the results achieved in accordance with the present invention.

In addition, the hardness data suggest that the product's hardness reaches acceptable levels between about 3.5% and about 5.5%, and most preferably between about 4% and about 5%, then drops off as the percentage of Mag increases.

Products Based Upon the Present Invention

Product in accordance with the present invention may be suitable for bulk storage, such as in silos or otherwise. It may also be bagged for storage and can even be transported or stored in relatively warmer climates. By contrast prior art formulations, such as the EB100 product and other mixtures of free fatty acids from tallow, palm or soy cannot.

Product Compression Properties

Figure 6:
FIG. 6 is a picture of a compression testing experimental setup used to assess the physical characteristics of compositions of the present invention.

FIG. 6 is a picture of a compression testing experimental setup used to assess the physical characteristics of compositions of the present invention.

Product in accordance with the present invention may be suitable for bulk storage, such as in silos or otherwise. It may also be bagged for storage and can even be transported or stored in relatively warmer climates. By contrast prior art formulations, such as the EB100 product and other mixtures of free fatty acids from tallow, palm or soy cannot.

The product of the present invention also features a controllable, increased onset melt point, as well as a controllable, increased hardness at all temperatures relative to free fatty acid mixtures of the prior art.

The product can be used as a feed supplement and may be formulated into fat supplementing animal feeds for livestock and the like. Examples may include dairy cow rations. The animal feeds may be rendered into particulate or pelletized form in accordance with and through the use of equipment and methods known and used in the art. By contrast, the pelleted feed applications compare favorably to the EB100 product and other mixtures of free fatty acids from tallow, palm or soy, which cannot be effectively pelleted.

Neutralization Data

Based upon the following raw data:

| | Raw Data | | |
|---|---|---|---|
| % Mag | Hardness @ 167 F. | % Neutralization | Target % Neutralization |
| 2.17 | 5 | 7.72 | 30 |
| 3.04 | 6 | 8.87 | 43.55 |
| 3.54 | 10 | 9.28 | 51.05 |
| 4.05 | 14 | 13.94 | 58.6 |
| 4.27 | 23 | 12.96 | 60 |
| 4.5 | 13 | 11.26 | 65.4 |
| 4.98 | 10 | 20.39 | 70 |
| 5.69 | 8 | 27.78 | 80 |
| 7.11 | 8 | 24.78 | 100 |
| 8.53 | 10 | 20.39 | 120 |

Figure 7:
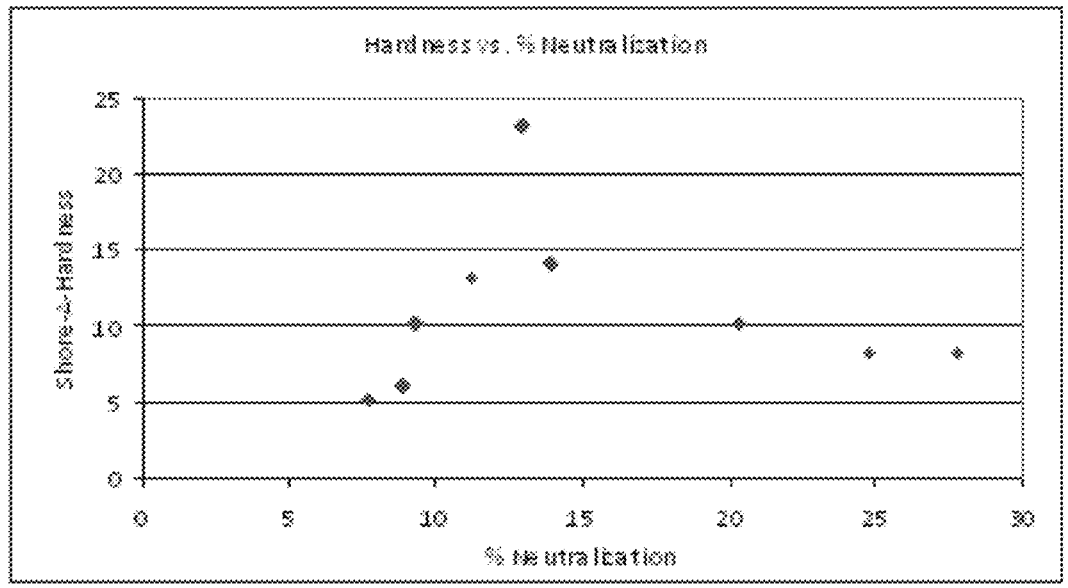
FIG. 7 is a graph showing the relationship between Shore A hardness and percent neutralization, in accordance with one embodiment of the present invention.

FIG. 7 is a graph showing the relationship between Shore A hardness and percent neutralization, in accordance with one embodiment of the present invention.

Figure 8:
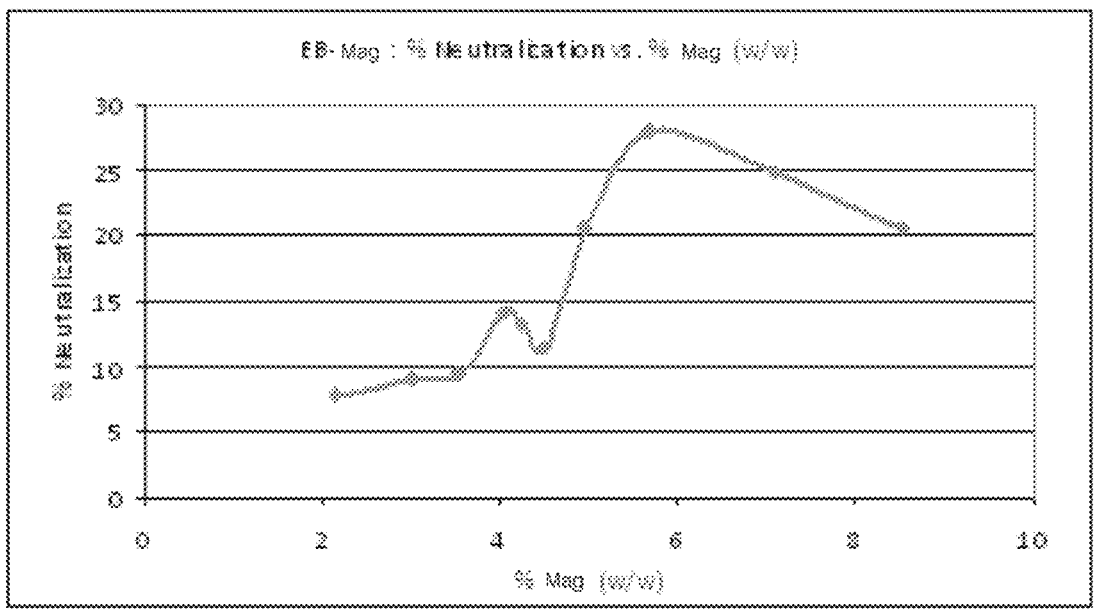
FIG. 8 is a graph showing the relationship between percent neutralization and magnesium oxide content, in accordance with one embodiment of the present invention.
Figure 13:
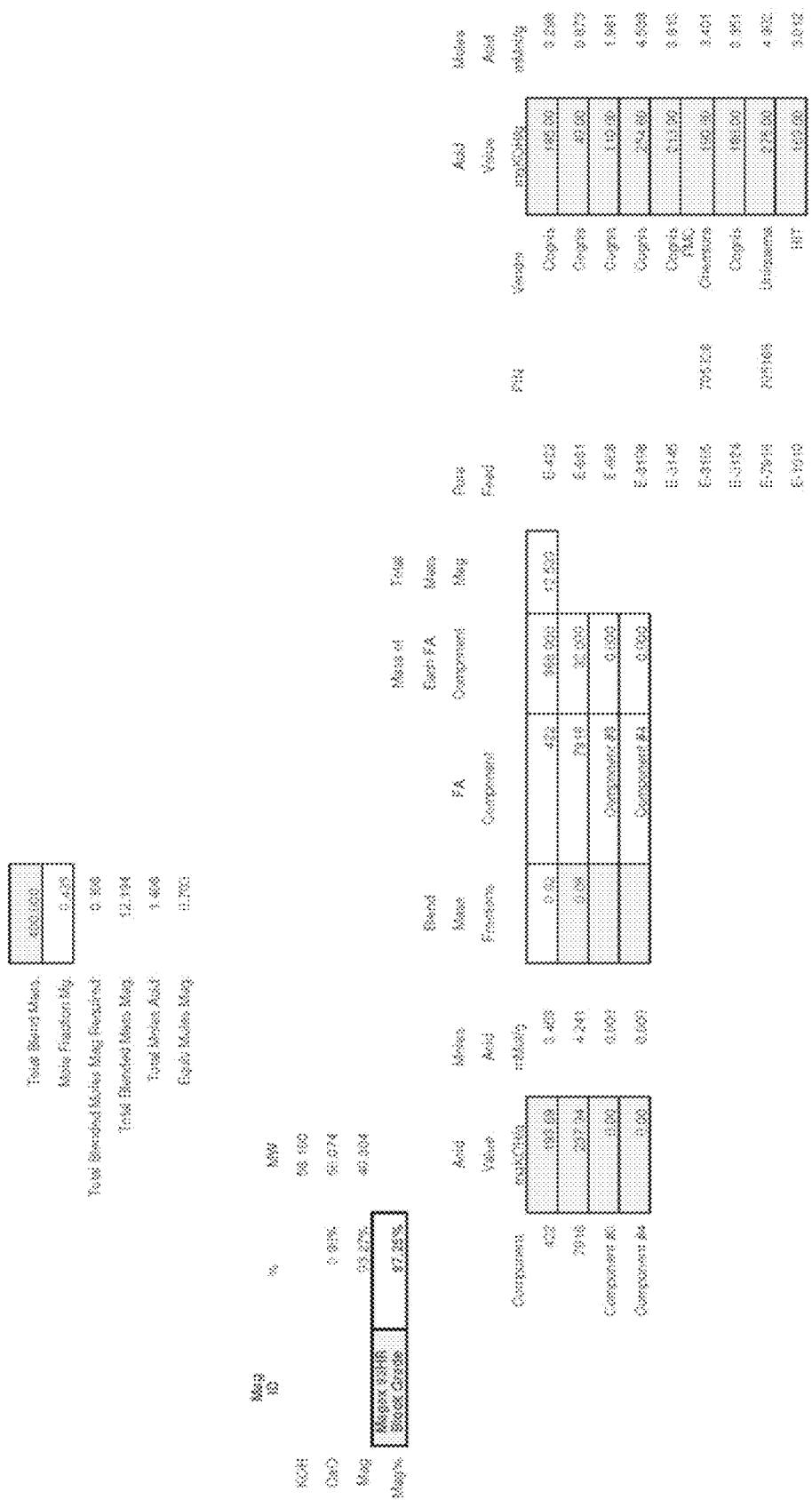
FIG. 13 is a laboratory notebook record of a production trial for the exemplary formulation.
Figure 14:
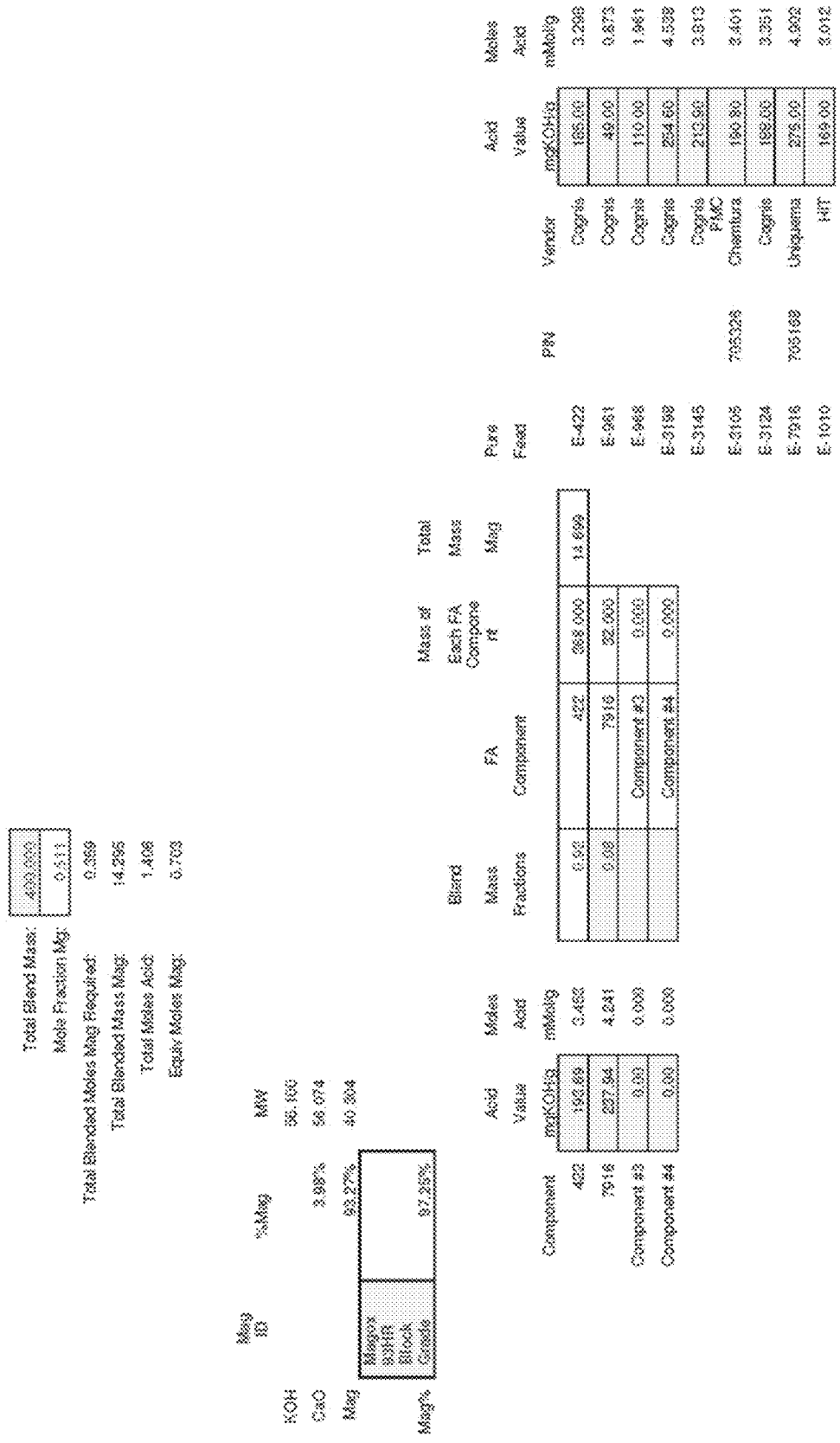
FIG. 14 is a laboratory notebook record of a production trial for the exemplary formulation.

FIG. 8 is a graph showing the relationship between percent neutralization and magnesium oxide content, in accordance with one embodiment of the present invention. It should be noted here that once the percentage of Mag increased, the test became less accurate due to mixing problems.

While specific configurations and arrangements are discussed, it should be understood that this is done for illustrative purposes only. A person skilled in the relevant art will recognize that other process and composition variations can be used without departing from the spirit and scope of the invention. It will be apparent to a person skilled in the relevant art that this invention can also be employed in a variety of other applications.

What is claimed is:
1. A method of producing a partially magnesium/neutralized free fatty acid mixture, the method comprising the steps:
   a. preparing a mixture of:
      i. an amount of a free fatty acid; and
      ii. an amount of a magnesium-containing material comprising a magnesium-containing basic compound adapted to form a magnesium salt of said fatty acid, said magnesium-containing material being present in an amount in the range of from about 25% to about 55% of the amount of a free fatty acid based upon the theoretical requirement to accomplish the total neutralization of all of fatty acid present; and b. maintaining said mixture at sufficient temperature and for sufficient amount of time so as to form a mixture of free fatty acid and partially magnesium/neutralized free fatty acid having an onset melt point of from 170° F. to 200° F.

2. A method according to claim 1 wherein said free fatty acid is selected from said group consisting of tallow and non-tallow fatty acids, and mixtures thereof.

3. A method according to claim 1 wherein said free fatty acid is selected from the group consisting of non-tallow fatty acids selected from the group consisting of fatty acids from palm oil, soy oil, fish oil, linseed oil and flax oil, and mixtures thereof.

4. A method according to claim 1 wherein said mixture is maintained at a temperature in the range of from about 255 degrees to about 300 degrees Fahrenheit during step (b).

5. A method according to claim 1 wherein said mixture is additionally subject to a prilling process.

6. A method according to claim 1 wherein said mixture is additionally subject to a flaking process.

7. A composition comprising a solidified particulate mixture of free fatty acid and a magnesium salt of a fatty acid, said magnesium salt of a fatty acid being present in a molar ratio amount in the range of from about 25% to about 55% of the amount of said free fatty acid based upon the theoretical requirement to accomplish the total neutralization of all of fatty acid present and having an onset melt point of from 170° F. to 200° F.

8. A composition according to claim 7, wherein said free fatty acid comprises tallow fatty acid, and said magnesium salt of a fatty acid comprises a magnesium salt of a tallow fatty acid.

9. A composition according to claim 7 wherein said free fatty acid is selected from the group consisting of tallow and non-tallow fatty acids, and mixtures thereof.

10. A composition according to claim 7 wherein said free fatty acid is selected from the group consisting of non-tallow fatty acids selected from the group consisting of fatty acids from palm oil, soy oil, fish oil, linseed oil and flax oil, and mixtures thereof.

11. A composition according to claim 7, wherein said mixture is a solid having an onset melt point of up to 170 degrees Fahrenheit and a hardness of at least about 15 shore A units at 170 degrees Fahrenheit.

12. A composition according to claim 7, wherein said mixture comprises magnesium equivalent to magnesium oxide present in an amount of from about 3.5% to about 5.5%, most preferably between about 4% and about 5%.

13. A livestock feed composition comprising (a) a solid particulate livestock feed material and (b) a solid particulate mixture of (i) free fatty acid and (ii) a magnesium salt of a fatty acid, said magnesium salt of a fatty acid being present in an amount in the range of from about 25% to about 55% of the amount of said free fatty acid based upon the theoretical requirement to accomplish the total neutralization of all of fatty acid present, and wherein said solid particulate mixture is a mixture of free fatty acid and partially magnesium/neutralized free fatty acid with an onset melt point of from 170° F. to 200° F.

14. A livestock feed composition according to claim 13, wherein said free fatty acid comprises tallow fatty acid, and said magnesium salt of a fatty acid comprises a magnesium salt of a tallow fatty acid.

15. A livestock feed composition according to claim 13 wherein said free fatty acid is selected from said group consisting of tallow and non-tallow fatty acids, and mixtures thereof.

16. A livestock feed composition according to claim 13 wherein said free fatty acid is selected from the group consisting of non-tallow fatty acids selected from the group consisting of fatty acids from palm oil, soy oil, fish oil, linseed oil and flax oil, and mixtures thereof.

* * * * *